US010029002B2

(12) United States Patent
Anderson et al.

(10) Patent No.: US 10,029,002 B2
(45) Date of Patent: *Jul. 24, 2018

(54) METHODS AND COMPOSITIONS FOR REDUCING THE ENVIRONMENTAL IMPACT OF ANIMAL WASTE

(71) Applicant: ELANCO US INC., Greenfield, IN (US)

(72) Inventors: David M. Anderson, Rockville, MD (US); Sergey Podkovyrov, Gaithersburg, MD (US); Yuefang Huang, Highland, MD (US); Kurt Schuster, Salisbury, MD (US); Jon Edward Ferrel, Frankfort, IN (US)

(73) Assignee: ELANCO US INC., Greenfield, IN (US)

( * ) Notice: Subject to any disclaimer, the term of this patent is extended or adjusted under 35 U.S.C. 154(b) by 69 days.

This patent is subject to a terminal disclaimer.

(21) Appl. No.: 15/142,745

(22) Filed: Apr. 29, 2016

(65) Prior Publication Data

US 2016/0235823 A1 Aug. 18, 2016

Related U.S. Application Data

(63) Continuation of application No. 14/347,705, filed as application No. PCT/US2013/025006 on Feb. 7, 2013, now Pat. No. 9,326,535.

(60) Provisional application No. 61/599,729, filed on Feb. 16, 2012.

(51) Int. Cl.
| | |
|---|---|
| *A61K 38/46* | (2006.01) |
| *C12N 9/16* | (2006.01) |
| *A23K 20/189* | (2016.01) |
| *A23K 50/75* | (2016.01) |
| *A23K 50/30* | (2016.01) |
| *A23K 50/60* | (2016.01) |

(52) U.S. Cl.
CPC .......... *A61K 38/465* (2013.01); *A23K 20/189* (2016.05); *A23K 50/30* (2016.05); *A23K 50/60* (2016.05); *A23K 50/75* (2016.05); *C12N 9/16* (2013.01); *C12Y 301/03001* (2013.01); *A23V 2002/00* (2013.01)

(58) Field of Classification Search
CPC ........ C12Y 301/03001; A23V 2002/00; A23V 2200/32; C12N 9/16; A23K 50/60; A23K 50/30; A23K 20/189; A23K 50/75; A61K 38/465
See application file for complete search history.

(56) References Cited

U.S. PATENT DOCUMENTS

| | | |
|---|---|---|
| 6,780,628 B2 | 8/2004 | Anderson et al. |
| 6,884,602 B2 | 4/2005 | Mueller et al. |
| 7,914,782 B2 | 3/2011 | Anderson et al. |
| 9,326,535 B2 * | 5/2016 | Anderson ...... C12Y 301/03001 |
| 2011/0171344 A1 | 7/2011 | Anderson et al. |

FOREIGN PATENT DOCUMENTS

| | | |
|---|---|---|
| CN | 101374544 A | 2/2009 |
| CN | 101735992 A | 6/2010 |
| CN | 102805268 A | 12/2012 |
| CN | 102839162 A | 12/2012 |
| WO | WO-97/41739 A1 | 11/1997 |

OTHER PUBLICATIONS

Bookstein C. et al., "The Bacillus subtilis 168 Alkaline Phosphatase III Gene: Impact of a phoAIII Mutation on Total Alkaline Phosphatase Synthesis", Journal of Bacteriology, Jul. 1990, vol. 172, No. 7, pp. 3730-3737. (Year: 1990).*
Hulett et al., 1991, "Bacillus subtilis Alkaline Phosphatases III and IV", Journal of Biological Chemistry, vol. 266, No. 2, pp. 1077-1084.
Chaidaroglou et al., 1989, "Alteration of aspartate 101 in the active site of *Escherichia coli* alkaline phosphatase enhances the catalytic activity", Protein Engineering, vol. 3, No. 2, pp. 127-132.
Li et al., 2014, *Paenibacillus lentus* sp. nov., a β-mannanolytic bacterium isolated from mixed soil samples in a selective enrichment using guar gum as the sole carbon source, Int. J. Syst. Evol. Microbiol. 64(Pt 4):1166-72. Epub Jan. 9, 2014.
Malo et al., 2014, Intestinal alkaline phosphatase promotes gut bacterial growth by reducing the concentration of luminal nucleotide triphosphates, Am. J. Physiol. Gastrointest. Liver Physiol. 306(10):G826-38. Epub Apr. 10, 2014.
Kornegay, "Digestion of phosphorous and other nutrients: the role of phytases and factors influencing their activity," in: Enzymes in Farm Animal Nutrition, eds. Bedford and Partridge, CAB International, 2001, pp. 237-271.
International Preliminary Report on Patentability dated Aug. 19, 2014 for PCT/US2013/025006 filed Feb. 7, 2013.
Elliot et al., "Factors Affecting Ammonia Release in Broiler Houses", 1982, Transactions of ASAE 25: 413-424.
Millan, "Oncodevelopmental expression and structure of alkaline phosphatase genes", Anticancer Res. 8(5A), 995-1004 (1988).
Harris, "The human alkaline phosphatases: What we know and what we don't know", Clin. Chim. Acta 186, 133-150 (1989).
Simpson et al., "The AttoPhos® System for Fluorescent Detection of Alkaline Phosphatase in an Enzyme-Linked Assay", Promega Notes 74: 7-9 (2000).
Du et al., "Artificial Evolution of an Enzyme Active Site: Structural Studies of Three Highly Active Mutants of *Escherichia coli* Alkaline Phosphatase", J. Mol. Biol. 316(4): 941-953 (2002).

(Continued)

*Primary Examiner* — Satyendra K Singh
(74) *Attorney, Agent, or Firm* — McAndrews, Held & Malloy, Ltd.

(57) ABSTRACT

Methods for reducing the environmental impact of animal waste are described. In particular embodiments, the methods comprise administering to an animal an enzyme, such as alkaline phosphatase, that is effective to reduce the amount of a detrimental compound, such as ammonia or phosphorous, that is present in or released from animal waste. Also provided is a method for increasing phosphorus digestion in an animal. Compositions suitable for use in such methods are also described.

22 Claims, No Drawings

(56) References Cited

OTHER PUBLICATIONS

Dealwis et al., "Crystallographic analysis of reversible metal binding observed in a mutant (Asp153→Gly) of *Escherichia coli* alkaline phosphatase," Biochem. 34: 13967-13973 (1995).
Koutsioulis et al., "Directed evolution on the cold adapted properties of TAB5 alkaline phosphatase", Protein Eng'g Design & Selection 21(5): 319-327 (2008).
Davidson, "Measurement of serum alkaline phosphatase", Enzyme Microb. Technol. 1: 9-14 (1979).
Gonzalez-Gil et al., "Detection and quantification of alkaline phosphatase in single cells of phosphorus-starved marine phytoplankton", Marine Ecol. Prog. Ser. 164: 21-35 (1998).
Sekiguchi et al., "Effects of amines and aminoalcohols on bovine intestine alkaline phosphatase activity", Enzyme Microb. Technol. 49: 171-76 (2011).
Mandana Behbahani, et al., "Investigation of biological behavior of Iranian indigenous phosphate solubilizing bacteria and determinant of colonization ability of potato roots by these bacteria isolation," Jounal of Medicinal Plants Research, vol. 3, No. 12, Dec. 1, 2009, pp. 1126-1133.
Ursula Konietzny, et al., "Molecular and catalytic properties of phytate-degrading enxymes (phytases)," International Journal of Food Science and Technology, Oct. 1, 2002, vol. 37, No. 7, pp. 791-812.
K. H. Nahm, "Efficient Feed Nutrient Utilization to Reduce Pollutants in Poultry and Swine Manure," Critical Reviews in Environmental Science and Technology, vol. 32, No. 1, Jan. 1, 2002, pp. 1-16.
Bijender Singh, et al., "Microbial phytases in phosphorus acquisition and plant growth pomotion," Physiology Molecular Biology of Plants; An International Journal of Functional Plant Biology, Spring-Verlag, India, May 7, 2011, vol. 17, No. 2, pp. 93-103.
J. Wang, et al., "Nucleotide sequence of Paenibacillus mucilaginosus (strain KNP414) alkaline phosphatase, F8FMM5," Sep. 21, 2011.
Scott A. Williams, et al., "The Relationship of Alkaline Phosphatase, CaATPase, and Phytase," Archives of Biochemistry and Biophysics, vol. 241, No. 1, Aug. 15, 1985, pp. 10-13.
International Search Report and Written Opinion dated May 2, 2013 for PCT/US2013/025006 filed Feb. 7, 2013.
Brenda: The Comprehensive Enzyme Information System [database online], Information on EC 3.1.3.1-alkaline phosphatase, Oct. 20, 2015. [retrieved on Dec. 19, 2017]. Retrieved from the Internet:< URL: https://web.archive.org/web/20151020052945/http://www.brenda-enzymes.org/enzyme.php?ecno=3.1.3.1>.

\* cited by examiner

SEQUENCE LISTING

```
<160> NUMBER OF SEQ ID NOS: 1

<210> SEQ ID NO 1
<211> LENGTH: 572
<212> TYPE: PRT
<213> ORGANISM: Bacillus lentus

<400> SEQUENCE: 1

Val Asn Lys Leu Leu Lys Gly Leu Ala Ile Gly Gly Ile Val Leu Ala
1               5                   10                  15

Val Val Ser Ala Gly Thr Leu Ala Val Ala Lys Glu Asn Ala Ser Arg
            20                  25                  30

Ala Glu Ser Ser Asn Gly Gln Ser Lys Asn Leu Ile Val Leu Ile Gly
        35                  40                  45

Asp Gly Met Gly Pro Ala Gln Val Ser Ala Ala Arg Tyr Phe Gln Gln
    50                  55                  60

His Lys Asn Asn Ile Asn Ser Leu Asn Leu Asp Pro Tyr Tyr Val Gly
65                  70                  75                  80

Gln Ala Thr Thr Tyr Ala Asp Arg Gly Glu Asp Gly His Ile Val
                85                  90                  95

Ser Gly Ile Val Thr Ser Ser Ala Ser Ala Gly Thr Ala Phe Ala Thr
            100                 105                 110

Gly Asn Lys Thr Tyr Asn Ala Ala Ile Ser Val Ser Asn Glu Asp Val
        115                 120                 125

Ser Arg Pro Phe Ala Ser Val Leu Glu Ala Ala Glu Leu Ser Gly Lys
    130                 135                 140

Ser Thr Gly Leu Val Thr Thr Ala Arg Ile Thr His Ala Thr Pro Ala
145                 150                 155                 160

Val Tyr Ala Ser His Val Arg Ser Arg Asp Asn Glu Asn Ala Ile Ala
                165                 170                 175

Phe Gln Tyr Leu Asp Ser Gly Ile Asp Val Leu Leu Gly Gly Gly Glu
            180                 185                 190

Ser Phe Phe Val Thr Lys Glu Glu Lys Gly Lys Arg Asn Asp Lys Asn
        195                 200                 205
```

-continued

```
Leu Leu Pro Glu Phe Glu Ala Lys Gly Tyr Lys Val Val Lys Thr Gly
    210             215                 220

Gln Ser Leu Lys Ser Leu Ser Ala Lys Asp Ala Lys Val Leu Gly Leu
225             230                 235                 240

Phe Gly Gly Ser His Ile Ala Tyr Val Pro Asp Arg Ser Asp Glu Thr
                245                 250                 255

Pro Ser Leu Ala Glu Met Thr Ser Lys Ala Leu Glu Ile Leu Ser Thr
                260                 265                 270

Asn Glu Asn Gly Phe Ala Ile Met Ile Glu Gly Arg Ile Asp His
                275                 280                 285

Ala Gly His Ala Asn Asp Phe Pro Thr Met Val Gln Glu Ala Leu Asp
            290                 295                 300

Phe Asp Glu Ala Phe Lys Val Ala Ile Asp Phe Ala Lys Lys Asp Gly
305                 310                 315                 320

Asn Thr Ser Val Val Val Thr Ala Asp His Glu Thr Gly Gly Leu Ser
                    325                 330                 335

Leu Ser Arg Asp Asn Ile Tyr Glu Leu Asn Val Asp Leu Trp Asn Lys
                340                 345                 350

Gln Lys Asn Ser Ser Glu Ser Leu Val Ser Ala Leu Asn Glu Ala Lys
                355                 360                 365

Thr Ile Ala Asp Val Lys Lys Ile Val Ser Asp Asn Thr Trp Ile Thr
    370                 375                 380

Asp Leu Thr Asn Glu Glu Ala Gln Tyr Ile Leu Asp Gly Asp Gly Ser
385                 390                 395                 400

Ser Tyr Lys Arg Glu Gly Gly Tyr Asn Ala Val Ile Ser Lys Arg Leu
                405                 410                 415

Leu Val Gly Trp Ser Gly His Gly His Ser Ala Val Asp Val Gly Val
                420                 425                 430

Trp Ala Tyr Gly Pro Ile Ala Asp Lys Val Lys Gly Gln Ile Asp Asn
            435                 440                 445

Thr Arg Ile Ala Thr Ala Ser Ala Glu Val Leu Gly Val Asp Leu Lys
    450                 455                 460

Lys Ala Thr Ala Asp Leu Gln Ser Lys Tyr Leu Tyr Pro Lys Phe Lys
465                 470                 475                 480

Ile Asn Arg Asn Lys Glu Val Leu Phe Pro Ala Lys Pro Leu Ala Glu
                485                 490                 495

Ala Leu Gly Gly Lys Tyr Gln Ala Ala Asn Gly Thr Ala Thr Ile Ser
                500                 505                 510

Gly Met Ser Gly Thr Ile Thr Val Asp Leu Asn Ala Lys Lys Ala Lys
            515                 520                 525

Leu Ser Gly Asn Ser Ser Ile Thr Ile Asp Val Asp Asn Asp Val
530                 535                 540

Leu Tyr Leu Pro Leu Thr Ala Phe Ser Gln Ile Thr Gly Gln Thr Leu
545                 550                 555                 560

Lys Trp Asp Ala Leu Ser Glu Arg Ile Met Leu Lys
                565                 570
```

METHODS AND COMPOSITIONS FOR REDUCING THE ENVIRONMENTAL IMPACT OF ANIMAL WASTE

CROSS-REFERENCE TO RELATED APPLICATION

The application is a continuation of U.S. application Ser. No. 14/347,705, filed on Mar. 27, 2014, which is a national stage of PCT/US2013/025006, filed Feb. 7, 2013, which claims the benefit of the filing date of U.S. Provisional Patent Application No. 61/599,729, filed Feb. 16, 2012. The entire disclosures of the aforesaid applications are incorporated herein by reference.

SEQUENCE LISTING

The instant application contains a Sequence Listing which has been submitted in ASCII format via EFS-Web and is hereby incorporated by reference in its entirety. Said ASCII copy, created on Apr. 11, 2016, is named 204257_0013_01_ST25.txt and is 5,315 bytes in size.

The present invention provides methods for reducing the environmental impact of animal waste. In particular, the invention provides methods comprising administering to an animal an enzyme that is effective to reduce the amount of a detrimental compound present in or released from animal waste, and compositions suitable for use in such methods. Also provided is a method for increasing phosphorus digestion in an animal.

Animal waste may contain or release one or more compounds that have a detrimental effect, such as a detrimental effect on the animal, on other animals, on humans, or on the environment. One such compound is ammonia ($NH_3$). Another such compound is phosphorous (P).

Atmospheric ammonia can have adverse effects on the environment, as well as on animal production performance, health, and welfare. Ammonia generation and emission in, for example, poultry housing, mostly result from the microbiological decomposition of poultry waste. Ammonia levels as low as 50 ppm can be detrimental to poultry, and such low levels may go unnoticed. Exposure to ammonia at 50 ppm can contribute to 5-10% of birds being runts, and can be associated with a loss of 0.5 pounds of meat per bird and/or a loss of 8 points of feed conversion.

There is a need, therefore, for methods of reducing the amount of a detrimental compound present in or released from animal waste, such as for reducing the ammonia and/or the phosphorous content of animal waste.

In accordance with some embodiments, there are provided methods for reducing the environmental impact of animal waste, comprising administering to an animal an effective amount of an enzyme that reduces the amount of a detrimental compound present in or released from animal waste. In accordance with some embodiments, there are provided methods for reducing the amount of ammonia in animal waste, comprising administering to an animal an effective amount of an enzyme that reduces the amount of ammonia present in or released from animal waste. In accordance with some embodiments, there are provided methods for reducing the amount of phosphorous in animal waste, comprising administering to an animal an effective amount of an enzyme that reduces the amount of phosphorous present in or released from animal waste. Also provided is a method for increasing phosphorus digestion in an animal, comprising administering an effective amount of alkaline phosphatase to the animal.

In accordance with any of these methods, the enzyme may be administered orally.

In accordance with any of these methods, the enzyme may be alkaline phosphatase.

In accordance with any of these methods, the animal may be a poultry or swine animal.

In accordance with any of these methods, the enzyme may be administered during one or more of the starter phase, the grower phase, and/or the finisher phase.

In accordance with any of these methods, the enzyme may be formulated in animal feed, such as a starter feed, a grower feed, or a finisher feed.

In accordance with any of these methods, the enzyme may be formulated in an animal feed additive.

In accordance with some embodiments, there are provided compositions suitable for oral administration to an animal, comprising an effective amount of an enzyme that reduces the amount of a detrimental compound present in or released from animal waste. In accordance with some embodiments, there are provided compositions suitable for oral administration to an animal, comprising an effective amount of an enzyme that reduces the amount of ammonia present in or released from animal waste. In accordance with some embodiments, there are provided compositions suitable for oral administration to an animal, comprising an effective amount of an enzyme that reduces the amount of phosphorous present in or released from animal waste.

In accordance with any of these compositions, the composition may comprise an orally acceptable carrier for the enzyme.

In accordance with any of these compositions, the enzyme may be alkaline phosphatase.

Any of these compositions may be suitable for administration to poultry or swine.

Any of these compositions may be an animal feed, such as a starter diet, a grower diet, or a finisher diet, or may be an animal feed additive.

As used in the following discussion, the terms "a" or "an" should be understood to encompass one or more, unless otherwise specified.

As used herein, the term "animal" refers to any animal, including humans and other animals, including companion animals such as dogs and cats, livestock, such as cows and other ruminants, buffalo, horses, swine (e.g., pigs or hogs), sheep, fowl or poultry (e.g., chicken, ducks, turkeys, and geese) and aquaculture animals (e.g., fish and shrimp and eels). A young animal is an animal which falls into the starter (or pre-starter) or grower category. Preferably, the young animal falls into the starter (or pre-starter) category. For swine, an animal less than 25 kilograms is also considered a young animal.

Described herein are methods comprising administering to an animal an enzyme that is effective to reduce the amount of a detrimental compound present in or released from animal waste, such as ammonia ($NH_3$) or phosphorous (P), and compositions suitable for use in such methods. The methods offer a number of advantages in the context of animal production, including poultry and swine production. For example, the methods may offer advantages such as reduced phosphate input into an animal production system, decreased ammonia in animal manure, reduced ventilation air requirements to dilute indoor ammonia concentration in animal housing (and associated energy savings), and reduced need to further treat exhaust air.

While not wanting to be bound by any theory, the results reported below indicate that the methods described herein may help animals (such as young broilers) utilize and digest the phosphorus that is present in their diets, which in turn may lead to better growth rate and less nutrient loss through excretion. Additionally or alternatively, the methods described herein may decrease $NH_3$ emission because the enzyme treatments may increase the metabolism and growth of favorable bacterial populations in the intestine, such that more of the excess nitrogen in the diet remains in the manure as bacterial protein instead of uric acid, which is typically degraded and emitted as $NH_3$. Moreover, both the lower pH and lower nitrogen content in manure of treated animals may deter and prevent the formation of gaseous $NH_3$ in the manure and reduce the $NH_3$ emission. The relationship between pH and degradation of uric acid (the major nitrogen source in poultry manure) has been reported such that a sharp increase in pH may be associated with a decrease in the uric acid content of poultry manure. Elliot & Collins, 1982, *Transactions of ASAE* 25: 413-24, indicated that high pH in the stored manure would result in the majority of nitrogen loss as $NH_3$. Additionally, reducing the phosphorus content of animal waste may impact other properties of the manure, such as the bacterial flora.

In specific embodiments, the enzyme is alkaline phosphatase (AP) (EC 3.1.3.1). Alkaline phosphatases occur in prokaryotic and eukaryotic organisms, including mammals (including humans). For example, alkaline phosphatase is naturally present in breast milk and intestines, and plays a key role in digestion and digestion regulation. Alkaline phosphatase has been studied for use in therapeutic contexts (e.g., the treatment of cancer, diabetes and weight loss). Comparison of the primary structures of various alkaline phosphatases showed a high degree of homology (25-30% homology between *E. coli* and mammalian). Milian, 1988 Anticancer Res. 8, 995-1004; Harris, 1989 Clin. Chim, Acta 186, 133-150. The alkaline phosphatase family includes the tissue-specific APs (placental AP (FLAP), germ cell AP (GCAP) and intestinal AP (TAP) and the non-tissue specific APs (TnAP) which are primarily located in the liver, kidney and bones. U.S. Pat. No. 6,884,602 reports the expression of alkaline phosphatase in yeast. Hundreds of microbial alkaline phosphatases have been described. See, e.g, BRENDA: The Comprehensive Enzyme Information System, on the web at www.brenda-enzymes.org/php/result flat.php?4?ecno=3.1.3.1. Moreover, organisms can be engineered to produce enzymes with desired properties, such as increased activity. See, e.g., Du et al. J. Mol. Biol. 316: 941-53 (2002); Dealwis Biochem. 34: 13967-73 (1995); Koutsioulis et al., Protein Eng'g Design & Selection 21: 319-27 (2008).

The invention also provides an alkaline phosphatase of SEQ ID NO:1, or an alkaline phosphatase having at least 70% sequence identity with SEQ ID NO:1. The following is SEQ ID NO:1:

```
VNKLLKGLAIGGIVLAVVSAGTLAVAKENASRAESSNGQSKNLIVLIGDG

MGPAQVSAARYFQQHKNNINSLNLDPYYVGQATTYADRGEDGGHIVSGIV

TSSASAGTAFATGNKTYNAAISVSNEDVSRPFASVLEAAELSGKSTGLVT

TARITHATPAVYASHVRSRDNENAIAFQYLDSGIDVLLGGGESFFVTKEE

KGKRNDKNLLPEFEAKGYKVVKTGQSLKSLSAKDAKVLGLFGGSHIAYVP

DRSDETPSLAEMTSKALEILSTNENGFAIMIEGGRIDHAGHANDFPTMVQ

EALDFDEAFKVAIDFAKKDGNTSVVVTADHETGGLSLSRDNIYELNVDLW

NKQKNSSESLVSALNEAKTIADVKKIVSDNTWITDLTNEEAQYILDGDGS
```

-continued
```
SYKREGGYNAVISKRLLVGWSGHGHSAVDVGVWAYGPIADKVKGQIDNTR

IATASAEVLGVDLKKATADLQSKYLYPKFKINRNKEVLFPAKPLAEALGG

KYQAANGTATISGMSGTITVDLNAKKAKLSGNSSSITIDVDNDVLYLPLT

AFSQITGQTLKWDALSERIMLK
```

The invention also provides alkaline phosphatases having at least 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity with SEQ ID NO:1. The invention also provides compositions containing at least one of the above alkaline phosphatases, as well as methods of using such an alkaline phosphatase for reducing the amount of one or more detrimental compounds present in or released from animal waste, increasing animal feed conversion rate, increasing animal feed efficiency, and/or increasing animal growth rate.

Sequence identity refers to a sequence that has a specified percentage of amino acid residues that are the same (i.e., share at least 70% identity, for example), when compared and aligned for maximum correspondence over a comparison window, or designated region as measured using a sequence comparison algorithms or by manual alignment and visual inspection.

In specific embodiments, the methods comprise administering to an animal an amount of an enzyme, such as alkaline phosphatase, effective to reduce the amount of ammonia ($NH_3$) or phosphorous present in or released from the animal's waste. The amount may vary depending on the animal, the animal's diet, and other factors, and can readily be determined by those skilled in the art using methods known in the art and illustrated in the examples. For example, the amount of ammonia ($NH_3$) and/or phosphorous present in or released from animal waste when given animals are grown under given conditions can be measured and compared to that present in or released from the animal waste of animals grown under comparable conditions, but also administered an amount of the enzyme, such as alkaline phosphatase. (In this regard, it may be advantageous to compare treated and control animals of the same age, as manure properties may change with age, as discussed in the examples below). A decrease in manure ammonia ($NH_3$) and/or phosphorous content or release associated with administration of the enzyme indicates that an effective amount of enzyme was administered.

The enzyme typically is administered orally. However, the invention also encompasses embodiments where the enzyme is administered by other routes to the intestines or digestive tract, in accordance with known practices, such as via suppositories.

The enzyme may be provided in any form suitable for oral administration, such as liquid, solid, powder, gel, etc. The enzyme may be administered alone, or may be formulated in any composition suitable for oral administration. In some embodiments, the composition that is suitable for oral administration is generally recognized as safe for oral administration to an animal. For example, a composition that is suitable for oral administration may contain only ingredients, and amounts of said ingredients, that are generally recognized as safe for oral administration to an animal, and does not contain any ingredients, or amounts of said ingredients, which are not generally recognized as safe for oral administration to an animal. Additionally or alternatively, a composition that is suitable for oral administration contains only ingredients, and amounts of said ingredients, that are allowed, or that are not prohibited, for oral administration to an animal, and does not contain any ingredients, or amounts of said ingredients, that are not allowed, or that are prohibited, for oral administration to an animal.

In some embodiments, the composition comprises an orally acceptable carrier for the enzyme. As used herein, "orally acceptable carrier" includes any physiologically acceptable carrier suitable for oral administration. Orally acceptable carriers include, without limitation, animal feed compositions, aqueous compositions, and liquid and solid compositions suitable for use in animal feed products and/or for oral administration to an animal, including liquid and solid animal feed additives. Suitable carriers are known in the art, and include those described in U.S. Pat. No. 6,780,628.

In some embodiments, the composition is an animal feed. As used herein, the term "animal feed" has its conventional meaning in the field of animal husbandry. For example, animal feed includes edible materials which are consumed by livestock for their nutritional value. Animal feed includes feed rations, e.g., compositions that meet an animal's nutritional requirements, and also include compositions that do not meet an animal's nutritional requirements. In some embodiments, the animal feed is a starter feed, formulated for use during the starter period. In other embodiments, the animal feed is a grower feed, formulated for use during the grower period. In other embodiments the animal feed is finisher feed used in the finishing period.

In specific examples of animal feed embodiment, the amount of enzyme (such as alkaline phosphatase) is at least about 10,000 international units (IU) per U.S. ton of feed, at least about 15,000 international units (IU) per U.S. ton of feed, at least about 20,000 international units (IU) per U.S. ton of feed, at least about 25,000 international units (IU) per U.S. ton of feed, at least about 30,000 international units (IU) per U.S. ton of feed, at least about 35,000 international units (IU) per U.S. ton of feed, at least about 40,000 international units (IU) per U.S. ton of feed, at least about 45,000 international units (IU) per U.S. ton of feed, at least about 50,000 international units (IU) per U.S. ton of feed, at least about 60,000 IU per ton of feed, at least about 70,000 IU per ton of feed, at least about 80,000 IU per ton of feed, at least about 90,000 IU per ton of feed, at least about 100,000 IU per ton of feed, at least about 200,000 IU per ton of feed, at least about 500,000 IU per ton of feed, or at least about 3,000,000 IU per ton of feed or higher.

In some embodiments, the amount of enzyme is in the range of about 25 to about 75 MU/ton (MU=124,000 IU). In some embodiments, the amount of enzyme is at least about 2 MU/ton (240,000 IU/ton or 264 IU/kg).

In other specific examples of animal feed embodiments, the amount of enzyme (such as alkaline phosphatase) is at least about 10 IU/kg feed, at least about 15 IU/kg feed, at least about 20 IU/kg feed, such as at least 20 IU/kg feed, at least at 25 IU/kg feed, at least 30 IU/kg feed, at least 35 IU/kg feed, at least at 40 IU/kg feed, at least at 45 IU/kg feed, at least 50 IU/kg feed, at least 550 IU/kg, or more.

Thus, in some embodiments, the invention provides an animal feed comprising an amount of an enzyme, such as alkaline phosphatase, that is effective to reduce the amount of a detrimental compound, such as ammonia ($NH_3$) and/or phosphorous, present in or released from animal waste, and/or to increase digestion of phosphorus.

The feed composition may be prepared by methods known in the art. For example, the enzyme can be added to the other feed ingredients at any stage during the manufacturing process, as deemed to be appropriate by those skilled in the art. In one embodiment, the enzyme is provided as a solution, such as a liquid enzyme concentrate that is added to other feed ingredients during the manufacturing process. Alternatively, an enzyme-containing solution is sprayed on to a substantially final form of the animal feed. In another embodiment, the enzyme is provided as a solid composition (such as a powder), such as a solid composition that is added to other feed ingredients during the manufacturing process. Exemplary methods for manufacturing enzyme-containing feed are described in WO 97/41739.

In some embodiments, the composition is other than an animal feed. For example, the composition may be a liquid composition other than an animal feed or a solid composition other than an animal feed. Such compositions may be suitable for direct administration to an animal or may be used as a feed additive (e.g., added to feed prior to feeding) or a feed supplement (including supplements that are diluted with other feed components prior to feeding and supplements that are offered to an animal on a free choice, separate basis). Examples of a liquid composition other than an animal feed include liquid enzyme concentrates, including liquid enzyme concentrates that are typically diluted or combined with other ingredients prior to oral administration to an animal.

In embodiments where the composition is a liquid composition other than an animal feed, such as an enzyme solution, the liquid composition or solution may comprise enzyme (such as alkaline phosphatase) in an amount that is at least about 40,000 international units (IU) per liter of solution, such as at least 40,000 IU/L, at least 50,000 IU/L, at least 60,000 IU/L, at least 70,000 IU/L, at least 80,000 IU/L, at least 90,000 IU/L, at least 100,000 IU/L, at least about 500,000 IU/L, at least about 600,000 IU/L, at least about 700,000 IU/L, at least about 800,000 IU/L, at least about 900,000 IU/L, at least about 1,000,000 IU/L, at least about 2,000,000 IU/L, at least about 5,000,000 IU/L, or at least about 200,000,000 IU/L.

In some embodiments, an amount of liquid composition other than an animal feed, such as about 500 mL or 1000 mL solution, is applied to or combined with an amount of feed, such as to a ton of feed, to arrive at feed formulations with enzyme levels described above. In other embodiments, an amount of liquid composition other than an animal feed is applied to or combined with an amount of feed to prepare an animal feed with an amount of enzyme effective to reduce the amount of a detrimental compound, such as ammonia ($NH_3$) and/or phosphorous, present in or released from animal waste, and/or to increase digestion of phosphorus.

In embodiments where the composition is a solid composition other than an animal feed, the composition may comprise enzyme (such as alkaline phosphatase) in an amount that is at least about 40,000 IU/kg, such as at least 40,000 IU/kg, at least 50,000 IU/kg, at least 60,000 IU/kg, at least 70,000 IU/kg, at least 80,000 IU/kg, at least 90,000 IU/kg, at least 100,000 IU/kg, at least 120,000 IU/kg, at least 140,000 IU/kg, at least 160,000 IU/kg, at least 180,000 IU/kg, at least 200,000 IU/kg, or at least 60,000,000 IU/kg, or more.

In some embodiments, an amount of a solid composition other than an animal feed is applied to or combined with an amount of feed to arrive at feed formulations with enzyme levels described above. In other embodiments, an amount of solid composition other than an animal feed is combined with an amount of feed to prepare an animal feed with an amount of enzyme effective to reduce the amount of a detrimental compound, such as ammonia ($NH_3$) and/or phosphorous, present in or released from animal waste, and/or to increase digestion of phosphorus.

In other embodiments, the enzyme is provided in a capsule or tablet form for oral ingestion.

As conventional in the art, the term "IU" or "international unit" refers to an amount of enzyme that will catalyze the transformation of 1 micromole of the substrate per minute under conditions that are optimal for the enzyme. As used herein "MU" (Million Chemgen Units)=120,000 IU. (1 IU=8.33 ChemGen U) Weight equivalents for many enzymes are known in the art and can be determined using standard assays. As known in the art, the selection of buffers and/or substrates can impact the units measured. Standard assays for alkaline phosphatase activity are known in the art. See, e.g., Davidson, Enzyme Microb. Technol. 1: 9-14 (1979); Gonzalez-Gil et al., Marine Ecol. Prog. Ser. 164: 21-35 (1998); Sekiguchi et al., Enzyme Microb. Technol. 49: 171-76 (2011); Simpson et al., Promega Notes 74: 7-9.

In one embodiment of the invention, a dry composition of the invention is present in an amount of more than 100 g per metric ton of complete feed. In one embodiment of the invention, a dry composition of the invention is present in an amount of more than 500 g per metric ton of complete feed.

In one embodiment of the invention, a dry composition of the invention is present in an amount of between 10 g and 30 g per metric ton of concentrated premix. In one embodiment of the invention, a dry composition of the invention is present in an amount of about 20 g per metric ton of concentrated premix.

In one embodiment of the invention, a liquid composition of the invention is present in an amount of less than 100 ml per metric ton of complete feed (liquid). In one embodiment of the invention, a liquid composition of the invention is present in an amount of 50-100 ml per metric ton of complete feed (liquid).

For use in any embodiment of the methods and compositions described herein, the enzyme, such as alkaline phosphatase, can be obtained from a commercial source. Alternatively, the enzyme (including alkaline phosphatase) can be obtained from microorganisms that produce enzymes, such as bacteria, fungi and yeast.

Additionally, the enzyme can be obtained using recombinant technology methods known in the art, by, for example, genetically engineering a host cell to produce an enzyme, e.g., causing transcription and translations of a gene encoding the enzyme. Using known amino acid sequences or known nucleotide sequences encoding those sequences, those skilled in the art can design suitable genes for recombinant expression of the enzyme. Additionally or alternatively, a nucleotide sequence encoding a known enzyme, such as alkaline phosphatase, can be used to probe a DNA library to identify other nucleotide sequences encoding enzymes suitable for use in the methods described herein. As known in the art, such a DNA library can be derived from a defined organism or population of organisms, or can be obtained from natural sources and thus represents DNA from microorganisms that are difficult to culture.

In any embodiment of the methods and compositions described herein, the enzyme, such as alkaline phosphatase, may be expressed by a plant that is used in animal feed. For example, corn could be genetically engineered to express alkaline phosphatase and the resulting genetically modified corn product could be used in feed. Production also can be effected with other genetically modified or classically modified systems such as bacteria, e.g., *E. coli, Bacillus* sp., *Lactobacillus*; yeast, e.g., *Pichia, Yarrow, Saccharomyces, Schizosaccharomyces* (e.g., *Schizosaccharomyces pomb, Hansenula. Kluyveromyces, Candida*), and other fungus, such as *Aspergillu, Rhizopus, Tricoderma, Humicola, Penicillium*, and *Humicola*. In specific embodiments, the enzyme, such as alkaline phosphatase, is obtained from *Bacillus lentus*.

In embodiments where a composition comprises a combination of enzymes, the enzymes may be produced individually, by separate organisms, or two or more of the enzymes may be produced by a single organism. For example, a single organism can be recombinantly engineered to produce two or more enzymes by methods known in the art.

As noted above, the invention includes methods for reducing the environmental impact of animal waste, comprising administering to an animal an effective amount of an enzyme that reduces the amount of a detrimental compound present in or released from animal waste. The invention also includes methods for reducing the amount of ammonia in animal waste, comprising administering to an animal an effective amount of an enzyme that reduces the amount of ammonia present in or released from animal waste. The invention also includes methods for reducing the amount of phosphorous present in or released from animal waste, comprising administering to an animal an effective amount of an enzyme that reduces the amount of phosphorous present in animal waste. The enzyme may be administered alone or in any composition described above, including an oral composition, such as animal feed, a liquid composition other than an animal feed, or a solid composition other than an animal feed. The animal may be any animal, including a human or a meat production animal, and may be a healthy animal or an animal suffering from infection or other disease or condition.

In any of these methods, the enzyme may be administered orally, and may be alkaline phosphatase.

In any of these methods, the animal may be a poultry animal, such as chickens, ducks, turkey, or geese, or a swine animal, such as pigs or hogs. In any of these methods, the enzyme may be administered during one or more of the starter phase, the grower phase, and/or the finisher phase, or at any or all stages.

In any of these methods, the enzyme may be formulated in animal feed, including in a starter feed, a grower feed, or a finisher feed. Alternatively, in any of these methods, the enzyme may be formulated in an animal feed additive.

As noted above, the invention also includes compositions suitable for oral administration to an animal, comprising an effective amount of an enzyme that reduces the amount of a detrimental compound present in or released from animal waste. The invention also includes compositions suitable for oral administration to an animal, comprising an effective amount of an enzyme that reduces the amount of ammonia present in or released from animal waste. The invention also includes compositions suitable for oral administration to an animal, comprising an effective amount of an enzyme that reduces the amount of phosphorous present in or released from animal waste. In any of these compositions, the composition may comprise an orally acceptable carrier for the enzyme. As noted above, the effective amount of enzyme may vary from animal to animal, and from enzyme to enzyme, but readily can be determined by those skilled in the art, as described above and illustrated in Example 3.

In any of these compositions, the enzyme may be alkaline phosphatase.

In any of these compositions, the composition may be suitable for administration to poultry, such as chickens, ducks, turkey, or geese, or to swine, such as pigs or hogs.

In any of these compositions, the composition may be an animal feed, such as a starter feed diet or a grower feed diet.

Alternatively, in any of these compositions, the composition may be an animal feed additive.

In any embodiments of the invention, one or more additional active ingredients may be employed. An example of an additional active ingredient is another enzyme, which may have the same or different properties of the enzymes of the invention.

The following examples further illustrate the invention, but the invention is not limited to the specifically exemplified embodiments.

EXAMPLE 1

Ammonia ($NH_3$) emissions of broiler manure samples from two feed additive treatments (Mannanase HT—"HT" and Alkaline Phosphatase "AP") were evaluated during a 6-week grow-out period. The mannanase HT was added at 60 MU/ton (240,000 IU/ton) and AP was added at an average of 141 MU/ton. The feed and water consumption, manure production and feed conversion of the broilers from three treatments (including control) were measured and reported. The nitrogen content, moisture content and pH of fresh manure samples were analyzed. The experiment was conducted in emission vessels with controlled air temperature and ventilation rate.

Feeding additives to broiler birds was shown to have the following impact on gaseous emissions and production performance:

(a) There was no significant difference in feed consumption, feed conversion, manure moisture content and pH observed for broilers fed with HT or AP as compared to birds fed the control diet, although manure from the AP diet showed lower pH than manure from the control group.

(b) There was no difference in $NH_3$ emission rate (ER) and cumulative emission between HT and control groups.

(c) The broilers fed the AP diet tended to have lower $NH_3$ emissions than the broilers fed control and HT diets.

(d) The $NH_3$ ER dramatically changed and increased exponentially from 28 and 42 days.

(e) The efficacy of $NH_3$ ER by the AP diet tended to be age-dependent during the three testing periods.

(f) The overall $NH_3$ ER rates for the 5 day storage periods were −7.4% from 35 day birds and 42.2% from 28 day birds in the AP group.

Materials and Methods

One hundred and seventeen 1-day-old female Ross 708 chicks were equally distributed into three brooding houses (7.4 ft×7.4 ft, W×L). The birds in each brooding house with a single pen were vaccinated with live Coccidia vaccine at 4-day age and had access to water and one of the three experimental diets (starter diet with HT, AP, or control). The brooding houses had the same temperature setup and lighting program. After 20-day age, 96 birds were transferred into grow-out cages in a ventilated poultry house (9 ft×9 ft, W×L) and were housed in groups of eight per cage (30 in×59 in, W×L).

Three grower diets were continuously fed to the birds for the grow-out. The eight birds in each cage were all from one of three treatments. After 35-day age, six birds were left in each cage to meet the animal welfare standards. A total of twelve cages were randomly assigned to three diets to minimize the location effect. The fresh manure from the birds in each cage was collected with manure pans for NH3 emission evaluation and analysis for five days on the days of 23, 28, 35, and 42.

Twelve 5-gallon (19-liter) emission vessels (EVs) were used to carry out the evaluation. Twelve manure samples of each batch were collected and 2.2 lb (1 kg) 2.2 lb (1 kg) manure samples were randomly placed in the twelve EVs with 50 $inch^2$ (324 $cm^2$) surface area of each sample, and measured for the gaseous emissions over a 5 day period with air temperature at 68° F. (20° C.) and air flow rate at 6.4 $ft^3$/hr (3 L/min). Both the air inlet and outlet were located in the air-tight lid. Teflon tubing (114 in or 0.635 cm diameter) was used in the emission vessel system. The vessels were operated under positive pressure. A diaphragm pump (Model DDL-80, Gast Inc., Benton Harbor, Mich.) was used to supply fresh air to the emission vessels. Flow rate of the fresh supply air was be controlled and measured with an air mass flow controller (0 to 100 LPM, with stainless steel wetted parts, Aalborg, Orangeburg, N.Y.). The supply air was connected to a distribution manifold where air was further divided via twelve identical flow meters (0.2 to 5 LPM, stainless steel valve, Dwyer Instruments, Inc., Michigan City, Ind.). Each vessel was equipped with a small stirring fan (12 VDC) located 2 in (5 cm) below the lid for 1.5 for uniform mixing of the headspace. Gas exhausted from the vessels was connected to a common 1.5 in (3.75 cm) PVC pipe that was routed to the building vent outlet. Samples of the exhaust air from each of the twelve vessels and the supply air were sequentially taken and analyzed at 5-minute intervals, with the first 3 min for stabilization and the last 2 min for measurement. This yielded a measurement cycle of 65 min for each vessel. The sequential sampling was achieved by controlled operation of twelve solenoid valves (Type 6014, 24V, stainless steel valve body. Burkert, Irvine, Calif.). The $NH_3$ concentration was measured with a photoacoustic multi-gas analyzer (INNOVA 1412, INNOVA, Denmark) that was challenged weekly and calibrated as needed with zero, and $NH_3$ calibration gases. Air temperature was measured with type T thermocouples (0.5° F. resolution). Analog outputs from the thermocouple, multi-gas analyzer, and the mass flow meter were sampled at 1-second interval and logged at 1-minute intervals into a measurement and control unit (USC-2416, Measurement Computing Corp., Norton, Mass.).

Seven weeks were used to complete the emission measurements. Frozen manure samples (0.25 lb/sample) were sent to a soil and water test lab at University of Delaware for manure nutrient and property analysis, which includes Total Kjeldahl Nitrogen (TKN), ammoniacal nitrogen, moisture, and pH. Statistical analysis was performed using JMP 9.0 (SAS Institute, Inc., Cary, N.C.). The dietary effect was considered significant at P-value ≤0.05.

Production Performances and Manure Properties

Production performances and fresh manure properties of the broilers from the three diets are shown in Tables 1 and 2.

TABLE 1

Manure properties (mean and standard error) of broiler birds fed with three diets of Mannanase HT, B: Alkaline Phosphatase (AP), and Ctrl: Control (n = 4).

| Bird age | Trt# | | MC*, % | $NH_4^+$—N, % (DM) | $NO_3^-$—N (DM) | TKN, % (DM) | pH |
|---|---|---|---|---|---|---|---|
| 23-d | A | Mean | 75.5 | 0.30 | 0.07 | 5.41 | 5.16 |
| | | S.E. | 1.1 | 0.06 | 0.01 | 0.35 | 0.07 |
| | B | Mean | 75.6 | 0.30 | 0.07 | 5.20 | 5.25 |
| | | S.E. | 0.7 | 0.04 | 0.02 | 0.28 | 0.05 |
| | Ctrl | Mean | 74.1 | 0.33 | 0.07 | 5.38 | 5.46 |
| | | S.E. | 0.4 | 0.02 | 0.03 | 0.16 | 0.26 |

TABLE 1-continued

Manure properties (mean and standard error) of broiler birds fed with three diets of Mannanase HT, B: Alkaline Phosphatase (AP), and Ctrl: Control (n = 4).

| Bird age | Trt[#] | | MC*, % | $NH_4^+$—N, % (DM) | $NO_3^-$—N (DM) | TKN, % (DM) | pH |
|---|---|---|---|---|---|---|---|
| 28-d | A | Mean | 73.2 | 0.33 | 0.08 | 6.31 | 5.35 |
| | | S.E. | 2.2 | 0.03 | 0.03 | 0.30 | 0.11 |
| | B | Mean | 73.6 | 0.35 | 0.04 | 5.52 | 5.31 |
| | | S.E. | 2.8 | 0.03 | 0.02 | 0.44 | 0.10 |
| | Ctrl | Mean | 72.9 | 0.42 | 0.12 | 5.77 | 5.40 |
| | | S.E. | 3.0 | 0.09 | 0.10 | 0.21 | 0.12 |
| 35-d | A | Mean | 73.9 | 0.73 | 0.12 | 6.99 | 5.69 |
| | | S.E. | 1.0 | 0.10 | 0.05 | 0.29 | 0.07 |
| | B | Mean | 76.3 | 0.82 | 0.09 | 7.29 | 5.57 |
| | | S.E. | 0.9 | 0.08 | 0.03 | 0.23 | 0.17 |
| | Ctrl | Mean | 76.7 | 0.91 | 0.07 | 7.06 | 5.90 |
| | | S.E. | 0.9 | 0.09 | 0.01 | 0.36 | 0.10 |
| 42-d | A | Mean | 79.1 | 1.18 | 0.09 | 8.68 | 6.37 |
| | | S.E. | 0.7 | 0.16 | 0.04 | 0.26 | 0.13 |
| | B | Mean | 79.5 | 1.61 | 0.03 | 8.41 | 6.38 |
| | | S.E. | 0.5 | 0.41 | 0.01 | 0.30 | 0.14 |
| | Ctrl | Mean | 78.5 | 1.44 | 0.07 | 7.66 | 6.55 |
| | | S.E. | 1.8 | 0.50 | 0.03 | 0.80 | 0.17 |

[#]A: Mannanase HT; B: Alkaline Phosphatase (AP); Ctrl: Control.
*MC: manure moisture content; DM: dry matter basis; TKN: total kjedahl nitrogen; pH: fresh manure pH.

TABLE 2

Production performances (mean and standard error) of broiler birds fed with three diets of A: Mannanase HT, B: Alkaline Phosphatase (AP), and Ctrl: Control (n = 4).

| Bird age | Trt[#] | | Manure*, g bird$^{-1}$d$^{-1}$ | Cumu feed*, kg bird$^{-1}$ | FCR* | Body*, kg bird$^{-1}$ |
|---|---|---|---|---|---|---|
| 23-d | A | Mean | 66.0 | 1.07 | 1.44 | 0.74 |
| | | S.E. | 2.0 | 0.00 | 0.03 | 0.02 |
| | B | Mean | 65.9 | 1.12 | 1.45 | 0.77 |
| | | S.E. | 3.6 | 0.00 | 0.03 | 0.02 |
| | Ctrl | Mean | 64.9 | 1.10 | 1.38 | 0.80 |
| | | S.E. | 4.5 | 0.00 | 0.03 | 0.02 |
| 28-d | A | Mean | 147.0 | 1.87 | 1.53 | 1.23 |
| | | S.E. | 5.5 | 0.01 | 0.05 | 0.04 |
| | B | Mean | 145.6 | 1.93 | 1.59 | 1.22 |
| | | S.E. | 11.0 | 0.02 | 0.01 | 0.02 |
| | Ctrl | Mean | 135.3 | 1.88 | 1.56 | 1.21 |
| | | S.E. | 8.3 | 0.00 | 0.03 | 0.04 |
| 35-d | A | Mean | 154.2 | 2.80 | 1.68 | 1.67 |
| | | S.E. | 12.8 | 0.02 | 0.03 | 0.02 |
| | B | Mean | 178.4 | 2.88 | 1.68 | 1.72 |
| | | S.E. | 10.9 | 0.02 | 0.02 | 0.03 |
| | Ctrl | Mean | 179.8 | 2.80 | 1.65 | 1.70 |
| | | S.E. | 14.5 | 0.03 | 0.01 | 0.03 |
| 42-d | A | Mean | 208.8 | 3.71 | 1.63 | 2.27 |
| | | S.E. | 7.0 | 0.02 | 0.01 | 0.01 |
| | B | Mean | 234.2 | 3.79 | 1.67 | 2.27 |
| | | S.E. | 20.7 | 0.02 | 0.01 | 0.01 |
| | Ctrl | Mean | 216.4 | 3.72 | 1.64 | 2.28 |
| | | S.E. | 12.9 | 0.03 | 0.03 | 0.06 |

[#]A: Mannanase HT; B: Alkaline Phosphatase (AP); Ctrl: Control.
*MC: manure moisture content; Manure: fresh manure production rate; Cumu feed: cumulative feed consumption; FCR: feed conversion ratio; Body: bird body weight.

There was no significant difference among the three diets for production performances and manure properties (P at 0.05). The nitrogen contents (ammoniacal nitrogen: $NH_4^+$—N and Total Kjeldahl Nitrogen: TKN) from the three diets were at similar levels (P>0.28). There was a trend that the HT and AP diets had slightly lower manure pH during the grow-out. The fresh manure of younger birds was more acidic than that from older birds.

Ammonia Emission and Reduction $NH_3$ daily ER and cumulative emissions over a 5-day storage period for the three diets are summarized and shown in Table 3.

TABLE 3

Mean (standard error) of ammonia daily emission rate (mg bird$^{-1}$ d$^{-1}$) and cumulative emissions (mg bird$^{-1}$) from broiler manure during a 5-d storage period (n = 4) with 10 air changes per hour (ACH) at 20° C.

| | | | Daily ER, mg bird$^{-1}$ d$^{-1}$ | | | | | Cumulative Emission, mg bird$^{-1}$ | | | | |
|---|---|---|---|---|---|---|---|---|---|---|---|---|
| | | | Storage time, day | | | | | | | | | |
| Age | Trt | | 1 | 2 | 3 | 4 | 5 | 1 | 2 | 3 | 4 | 5 |
| 23-d | A | Mean | 0.07 | 0.53 | 3.16 | 6.72 | 8.50 | 0.07 | 0.61 | 3.77 | 10.5 | 19.0 |
| | | S.E. | 0.01 | 0.21 | 0.91 | 1.06 | 0.76 | 0.01 | 0.24 | 1.14 | 2.17 | 2.85 |
| | B | Mean | 0.06 | 0.26 | 1.29 | 3.20 | 5.25 | 0.06 | 0.32* | 1.61* | 4.81 | 10.1 |
| | | S.E. | 0.00 | 0.07 | 0.41 | 1.07 | 1.40 | 0.00 | 0.07 | 0.48 | 1.57 | 3.00 |
| | Ctrl | Mean | 0.13 | 0.53 | 3.13 | 5.42 | 7.11 | 0.13 | 0.67 | 3.80 | 9.22 | 16.3 |
| | | S.E. | 0.02 | 0.13 | 0.83 | 0.95 | 0.88 | 0.00 | 0.07 | 0.47 | 1.55 | 2.96 |
| 28-d | A | Mean | 0.26 | 1.23 | 5.10 | 10.9 | 17.4 | 0.26 | 1.49 | 6.60 | 17.5 | 34.9 |
| | | S.E. | 0.02 | 0.24 | 1.28 | 2.32 | 2.92 | 0.02 | 0.31 | 1.65 | 4.04 | 7.04 |
| | B | Mean | 0.27 | 1.01 | 2.60 | 4.97* | 10.2* | 0.27 | 1.29 | 3.88 | 8.86 | 19.0 |
| | | S.E. | 0.04 | 0.22 | 1.27 | 2.58 | 3.10 | 0.03 | 0.29 | 1.61 | 4.29 | 7.42 |
| | Ctrl | Mean | 0.27 | 1.53 | 4.10 | 8.37 | 18.6 | 0.27 | 1.79 | 5.90 | 14.3 | 32.9 |
| | | S.E. | 0.03 | 0.58 | 2.25 | 2.98 | 2.44 | 0.03 | 0.66 | 2.64 | 5.22 | 6.73 |
| 35-d | A | Mean | 3.27 | 21.4 | 36.0 | 48.2 | 62.7 | 3.27 | 24.7 | 60.7 | 108.9 | 171.6 |
| | | S.E. | 1.30 | 5.91 | 7.85 | 9.68 | 13.7 | 1.21 | 7.47 | 15.2 | 25.1 | 38.9 |
| | B | Mean | 2.70 | 18.2 | 36.2 | 52.0 | 68.7 | 2.70 | 20.9 | 57.1 | 109.1 | 177.9 |
| | | S.E. | 0.79 | 3.59 | 7.64 | 14.5 | 22.8 | 0.75 | 4.66 | 12.7 | 28.2 | 51.2 |
| | Ctrl | Mean | 9.82 | 33.9 | 37.6 | 39.3 | 44.8 | 9.82 | 43.7 | 81.4 | 120.7 | 165.6 |
| | | S.E. | 3.31 | 4.08 | 1.92 | 1.91 | 2.18 | 3.35 | 7.29 | 8.91 | 9.9 | 10.7 |

TABLE 3-continued

Mean (standard error) of ammonia daily emission rate (mg bird$^{-1}$ d$^{-1}$)
and cumulative emissions (mg bird$^{-1}$) from broiler manure during a
5-d storage period (n = 4) with 10 air changes per hour (ACH) at 20° C.

| | | | Daily ER, mg bird$^{-1}$ d$^{-1}$ | | | | | Cumulative Emission, mg bird$^{-1}$ | | | | |
|---|---|---|---|---|---|---|---|---|---|---|---|---|
| | | | Storage time, day | | | | | | | | | |
| Age | Trt | | 1 | 2 | 3 | 4 | 5 | 1 | 2 | 3 | 4 | 5 |
| 42-d | A | Mean | 13.8 | 46.9 | 66.9 | 77.1 | 81.4 | 13.8 | 60.7 | 127.6 | 204.7 | 286.1 |
| | | S.E. | 3.62 | 6.80 | 6.61 | 6.61 | 10.8 | 2.04 | 3.66 | 10.7 | 25.4 | 40.3 |
| | B | Mean | 15.1 | 43.8 | 47.9 | 57.3 | 62.3 | 15.1 | 58.9 | 106.8 | 164.1 | 226.4 |
| | | S.E. | 4.50 | 7.82 | 6.66 | 8.81 | 11.4 | 4.57 | 9.91 | 22.1 | 41.1 | 62.3 |
| | Ctrl | Mean | 23.0 | 48.2 | 60.9 | 63.3 | 63.7 | 23.0 | 71.2 | 132.1 | 195.4 | 259.1 |
| | | S.E. | 9.84 | 11.0 | 9.51 | 9.67 | 11.5 | 10.1 | 20.8 | 30.0 | 38.2 | 47.1 |

The NH$_3$ ERs were the lowest over the 5-day storage period for the AP diet at 23 and 28 days. There was no difference on NH$_3$ ER and cumulative emission between HT and control diets. There were some significant differences between the AP and control diets (P<0.05). For instance, the NH$_3$ ERs on the 4th and 5th day from 28-day birds were significantly lower (P=0.02). The NH$_3$ ER dramatically changed and increased exponentially from 28 and 42 days. For example, the ER from 35-day birds on the 2nd day of the 5-day storage was 18.2 mg/bird/day, which was much higher than the ER (1.01 mg/bird/day) from 28-day birds. This change could be related to the increasing trend of manure pH from less than 5.5 to 6.5. The ammoniacal N is in the form of NH$_4^+$, which is not volatile with low pH.

The efficacy of NH$_3$ emission reduction by the AP diet tended to be age-dependent during the testing period. The efficacy of NH$_3$ emission reduction by the AP diet decreased with increasing bird age (Table 4).

TABLE 4

Reduction rate (percentage) of cumulative ammonia
emissions during a 5-d storage period (n = 4)

| | | Storage time, day | | | | |
|---|---|---|---|---|---|---|
| Treatment | Bird age | 1 | 2 | 3 | 4 | 5 |
| A | 23-d | 46.8 | 9.4 | 0.9 | -13.8 | -16.3 |
| | 28-d | 1.7 | 16.8 | -11.9 | -22.7 | -6.0 |
| | 35-d | 66.7 | 43.5 | 25.4 | 9.8 | -3.6 |
| | 42-d | 39.8 | 14.7 | 3.4 | -4.8 | -10.4 |
| B | 23-d | 56.8 | 52.9 | 57.7 | 47.9 | 38.4 |
| | 28-d | -2.1 | 28.2 | 34.1 | 37.9 | 42.2 |
| | 35-d | 72.6 | 52.2 | 29.8 | 9.6 | -7.4 |
| | 42-d | 34.2 | 17.2 | 19.1 | 16.0 | 12.6 |

In comparison, NH$_3$ ER reduction varied from 57.7% from 23-day birds, to 19.1% from 42-day birds for the AP diet after storage time. The overall NH$_3$ emission reduction rates for the 5-day period were -7.4% from 35-day birds and 42.2% from 28-day birds for the AP regimens.

The outcome of the variable dietary efficacy could have stemmed from changes in manure properties, especially moisture content and pH, as the microbial activities varied considerably. Under the production condition, the broiler houses with young birds tend to have higher NH$_3$ concentration at bird level due to limited ventilation, conserving heating energy, and lowering gas usage. Lowering NH$_3$ emissions from broiler houses with young birds will help to establish healthy flocks and reduce the risk of disease breakout related to high NH$_3$ concentration.

EXAMPLE 2

In this study, ammonia (NH$_3$) emissions of broiler chickens fed with an enzyme feed additive (Alkaline Phosphatase—AP) were evaluated during a 30-day grow-out period. The broilers were brooded on wood shavings until 12-days of age and moved into cages for rest of the grow-out. Fresh manure was collected on days 14, 22, and 30, and tested for NH$_3$ emissions in emission vessels with controlled air temperature and ventilation rate. The feed and water consumption, manure production, and feed conversion of the broilers were measured and reported. The nutrient content, moisture, and pH of the fresh manure samples were analyzed. Feeding enzyme additives to broiler birds was shown to have the following impact on gaseous emissions and production performance:

(a) AP diet improved broiler growth and feed conversion ratio at ages of 22- and 30 days.
(b) AP diet reduced manure pH at 22-days and lowered phosphorus by 6 and 7% at 14- and 22-days.
(c) NH$_3$ emission was significantly reduced by 23.8% over a 4-day period at 14-days.
(d) Overall NH$_3$ emission reduction rates for the 4-day period were 5.9% from 30-day birds and 30.7% from 22-day birds.

Materials and Methods

Four temperature controlled houses (7.4 ft×7.4 ft, W×L) with new wood shavings were used for brooding. Each brooding house was equipped with one 1.5 kW space heater and 150 W heat lamp with one cup drinker (1 ft diameter) and one feeder (1 ft diameter). Two groups (3-days apart) of 148 day-old female Ross 708 female chicks from a same breeder flock were collected and equally distributed into the two brooding houses (74 birds per house). The birds in each brooding house with a single pen were vaccinated with live Coccidia vaccine and had access to water and two experimental diets (AP and control) with the AP added at 60 MU/ton to both starter and grower diets. The brooding houses had identical temperature and lighting programs. The birds were fed ad libitum with two diets: control and AP. After 12 days, groups of 12 birds per cage were transferred to grow-out cages (30 in×30 in, W×L) in two identical houses (9 ft×9 ft, W×L), 12 cages per house. Each cage had two nipple drinkers, one trough drinker (2.5 in×30 in, W×L), and one trough feeder (5 in×30 in, W×L). The bird numbers were reduced to 8 birds per cage on 22-day age. A total of 24 cages were assigned to the two houses by random block design to minimize the house effect. The birds in the same house were of the same age. The light program was 23:1 hour (Light:Dark) for the brooding period and 24 hour light for the rest of grow-out. The temperature of each house was measured and recorded by a temperature logger (HOBO U23, Onset Comp., Pocasset, Mass.) with 5 minute intervals. The birds were weighed on days 0, 12, 14, 22, and 30. The feed usage was recorded daily and feed conversion ratio (FCR) was calculated. The starter diet was as follows:

| INGREDIENT | AMOUNT |
|---|---|
| Corn US #2 | 1000 |
| Soybean Meal Hi Pro 48% CP | 513 |
| Meat ML 55/Blend 52 | 110 |
| DDGS | 160 |
| Bakery Dex | 60 |
| Canola ML | 50 |
| SUB-TOTAL | 1893 |
| Corn Micro Flush | 18.05 |
| Limestone | 13.00 |
| Dicalcium Phosphate 18.5% P | 11.00 |
| BioLys 50% | 7.90 |
| DL-Methionine | 5.54 |
| S-Carb-30 | 3.00 |
| Salt | 1.20 |
| HyD 83.3 | 0.60 |
| Choline Chloride 60% | 1.52 |
| Tmin + EDDI | 1.25 |
| Vitamins 2X | 0.60 |
| Quantum Phytase 2500 D | 0.44 |
| Mintrex-Cu | 0.40 |
| Poultry Fat Pet Food Grade | 42.50 |
| TOTAL BATCH WEIGHT | 2000.00 |

The grower diet was as follows:

| INGREDIENT | AMOUNT |
|---|---|
| Corn US #2 | 1000 |
| Soybean Meal Hi Pro 48% CP | 513 |
| Meat ML 55/Blend 52 | 110 |
| DDGS | 160 |
| Bakery Dex | 60 |
| Canola ML | 50 |
| SUB-TOTAL | 1893 |
| Corn Micro Flush | 18.05 |
| Limestone | 13.00 |
| Dicalcium Phosphate 18.5% P | 11.00 |
| BioLys 50% | 7.90 |
| DL-Methionine | 5.54 |
| S-Carb-30 | 3.00 |
| Salt | 1.20 |
| HyD 83.3 | 0.60 |
| Choline Chloride 60% | 1.52 |
| Tmin + EDDI | 1.25 |
| Vitamins 2X | 0.60 |
| Quantum Phytase 2500 D | 0.44 |
| Mintrex-Cu | 0.40 |
| Poultry Fat Pet Food Grade | 42.50 |
| TOTAL BATCH WEIGHT | 2000.00 |

Stainless steel manure pans were used to collect the fresh manure from the cages in Block 1 on days 12, 20, and 28, and from the cages in Block 2 on days 13, 21, and 29, for a 2-day period. Twelve 2.2 lb (1 kg) manure samples were taken for $NH_3$ emission test on days 14, 22, and 30 for Block 1, and days 15, 23, and 31 for Block 2, respectively. Additional 0.5 lb samples were stored in a −20° C. freezer and sent to a certified lab (Midwest Laboratories, Omaha, Nebr.) for nutrient and property analysis, which included total Kjeldahl nitrogen (TKN), ammonia nitrogen ($NH_3$—N), phosphorus (reported as $P_2O_5$), potassium ($K_2O$), sulfur (S), moisture, and pH.

Twelve 5-gallon (19-liter) emission vessels (EVs) were used to carry out the $NH_3$ emission evaluation. Twelve manure samples of each block were collected and 2.2-lb manure samples were randomly placed in the twelve EVs with 50 inch$^2$ (324 cm$^2$) surface area of each sample, and measured for the gaseous emissions over a 4-day period with air temperature at 75° F. (24 C) and air flow rate at 6.4 ft$^3$/hr (3 L/min). Both the air inlet and outlet were located in the air-tight lid. Teflon tubing (0.635 cm or ¼ in. diameter) was used in the emission vessel system. The vessels were operated under positive pressure. A diaphragm pump (Model DDL-80, Gast Inc., Benton Harbor, Mich.) was used to supply fresh air to the emission vessels. Flow rate of the fresh supply air was be controlled and measured with an air mass flow controller (0 to 100 LPM, with stainless steel wetted parts, Aalborg, Orangeburg, N.Y.). The supply air was connected to a distribution manifold where air was further divided via twelve identical flow meters (0.2 to 5 LPM, stainless steel valve, Dwyer Instruments, Inc., Michigan City, Ind.). Each vessel was equipped with a small stirring fan (12 VDC) located 2 in (5 cm) below the lid for uniform mixing of the head space. Gas exhausted from the vessels was connected to a common 1.5 in (3.75 cm) PVC pipe that was routed to the building vent outlet. Samples of the exhaust air from each of the twelve vessels, the supply air and the ambient air were sequentially taken and analyzed at 5 minute intervals, with the first 3 minutes for stabilization and the last 2 minutes for measurement. This yielded a measurement cycle of 65 minutes for each vessel. The sequential sampling was achieved by controlled operation of twelve solenoid valves (Type 6014, 24V, stainless steel valve body, Burkert, Irvine, Calif.). The $NH_3$ concentration was measured with a photoacoustic multi-gas analyzer (INNOVA 1412, INNOVA, Denmark) that was challenged weekly and calibrated as needed with zero, and $NH_3$ calibration gases. Air temperature was measured with type T thermocouples (0.5° F. resolution). Analog outputs from the thermocouple, multi-gas analyzer, and the mass flow meter were sampled at 1-s intervals and logged at 1-min intervals into a measurement and control unit (USB-2416, Measurement Computing Corp., Norton, Mass.).

The data from the two blocks at the similar ages were pooled and analyzed for the dietary and age effect. Therefore, three age groups at 14-, 22-, and 30-days were used to represent 14- to 15-day, 22- to 23-day, and 30- to 31-day, respectively. Statistical analysis was performed using JMP 9.0 (SAS Institute, Inc., Cary, N.C.). The dietary effect was considered significant at P-value ≤0.05.

Production Performances and Manure Properties

Production performances of the broilers from the two diets are shown in Table 5.

TABLE 5

Production performances and manure properties (mean and standard error) of broiler birds fed with two diets of Ctrl: Control, and Trt: Alkaline Phosphatase (AP) (n = 12).

| Bird age | Trt[#] | | MC*, % | DM, g bird$^{-1}$d$^{-1}$ | Manure*, g bird$^{-1}$d$^{-1}$ | Cumu feed*, kg bird$^{-1}$ | FCR* | Body*, kg bird$^{-1}$ |
|---|---|---|---|---|---|---|---|---|
| 14-d | Ctrl | Mean | 72.0 | 16.82 | 60.2 | 0.58 | 1.35 | 0.43 |
|  |  | S.E. | 0.93 | 0.78 | 2.40 | 0.02 | 0.05 | 0.01 |
|  | Trt | Mean | 73.0 | 17.49 | 65.7 | 0.60 | 1.35 | 0.44 |
|  |  | S.E. | 0.95 | 0.55 | 3.15 | 0.01 | 0.01 | 0.00 |
| 22-d | Ctrl | Mean | 73.3 | 24.5 | 92.5 | 1.24 | 1.42 | 0.86 |
|  |  | S.E. | 1.14 | 0.94 | 3.74 | 0.03 | 0.04 | 0.01 |
|  | Trt | Mean | 72.6 | 24.2 | 88.9 | 1.27 | 1.45 | 0.88 |
|  |  | S.E. | 0.95 | 0.67 | 2.79 | 0.02 | 0.02 | 0.01 |
| 30-d | Ctrl | Mean | 77.6 | 33.1 | 149.8 | 2.02 | 1.36 | 1.48 |
|  |  | S.E. | 0.73 | 0.71 | 6.43 | 0.01 | 0.01 | 0.01 |
|  | Trt | Mean | 77.5 | 34.1 | 153.5 | 2.01 | 1.31 | 1.54 |
|  |  | S.E. | 0.86 | 0.73 | 6.10 | 0.01 | 0.02 | 0.02 |

[#]Ctrl: Control; Trt: Alkaline Phosphatase (AP).
*MC: moisture content; DM: dry manure production rate Manure: fresh manure production rate; Cumu feed: cumulative feed consumption; FCR: feed conversion ratio; Body: bird body weight.

There was no significant difference from AP diet on manure production rate at either age. The birds with AP diet had better growth rate at ages of 22- and 30-day (P=0.037 and 0.006). At 30-day age, the AP group had better FCR (1.31 vs. 1.36) than the control group (P=0.03).

The manure properties of the two diets are presented in Table 6.

TABLE 6

Nutrient content (percentage of dry matter basis) and pH (mean and standard error) of fresh manure from two diets of Ctrl: Control, and Trt: Alkaline Phosphatase (AP) (n = 12).

| Bird age | Trt[#] | | pH | $NH_3$—N*, % | TKN*, % | $P_2O_5$*, % | $K_2O$*, % | S*, % |
|---|---|---|---|---|---|---|---|---|
| 14-d | Ctrl | Mean | 5.77 | 0.25 | 5.29 | 2.36 | 2.91 | 0.62 |
|  |  | S.E. | 0.05 | 0.01 | 0.32 | 0.06 | 0.06 | 0.02 |
|  | Trt | Mean | 5.73 | 0.22 | 5.09 | 2.22$^a$ | 2.89 | 0.62 |
|  |  | S.E. | 0.13 | 0.01 | 0.22 | 0.04 | 0.04 | 0.01 |
| 22-d | Ctrl | Mean | 6.37 | 0.37 | 5.46 | 2.27 | 2.84 | 0.61 |
|  |  | S.E. | 0.13 | 0.03 | 0.24 | 0.05 | 0.05 | 0.01 |
|  | Trt | Mean | 5.98$^a$ | 0.30 | 5.34 | 2.12$^a$ | 2.91 | 0.60 |
|  |  | S.E. | 0.08 | 0.02 | 0.15 | 0.04 | 0.04 | 0.01 |
| 30-d | Ctrl | Mean | 6.25 | 0.75 | 5.50 | 2.20 | 2.81 | 0.60 |
|  |  | S.E. | 0.15 | 0.07 | 0.23 | 0.05 | 0.08 | 0.01 |
|  | Trt | Mean | 6.44 | 0.69 | 5.61 | 2.17 | 2.74 | 0.59 |
|  |  | S.E. | 0.17 | 0.07 | 0.19 | 0.06 | 0.07 | 0.01 |

[#]Ctrl: Control; Trt: Alkaline Phosphatase (AP).
*$NH_3$—N: ammonia nitrogen; TKN: total Kjeldahl nitrogen; S: sulfur.

It shows that the AP diet reduced manure pH at 22-d (P=0.05) and lowered phosphorus (2.22 vs. 2.36% and 2.12 vs. 2.27%) at 14-day (P=0.05) and 22-day (P=0.02). In addition, there is a trend that AP diet could cause less $NH_3$—N and TKN in the manure.

These results indicate that the AP diet could help young broilers utilize and digest the nitrogen and phosphorus, which leads to better growth rate and less nutrient loss through excretion. Both lower pH and nitrogen content in manure could deter and prevent the formation of gaseous $NH_3$ in the manure and reduce the $NH_3$ emission.

Ammonia Emissions $NH_3$ daily emission rate (ER) and cumulative emissions over a 4-day period for the two diets are summarized and shown in Table 7.

TABLE 7

Mean (standard error) of ammonia daily emission rate (mg bird$^{-1}$ d$^{-1}$) and cumulative emissions (mg bird$^{-1}$) from broiler manure during a 4-d storage period (n = 12) with 10 air changes per hour (ACH) at 24° C.

| | | | Daily ER, mg bird$^{-1}$ d$^{-1}$ | | | | Cumulative Emission, mg bird$^{-1}$ | | | |
|---|---|---|---|---|---|---|---|---|---|---|
| | | | Storage time, day | | | | | | | |
| Age | Trt | | 1 | 2 | 3 | 4 | 1 | 2 | 3 | 4 |
| 14-d | Ctrl | Mean | 0.82 | 3.30 | 5.21 | 5.99 | 0.51 | 3.71 | 9.64 | 13.6 |
|  |  | S.E. | 0.24 | 0.30 | 0.55 | 0.59 | 0.06 | 0.36 | 0.92 | 1.33 |
|  | Trt | Mean | 0.67 | 2.59* | 3.88* | 4.48* | 0.45 | 2.95* | 7.43* | 10.4** |
|  |  | S.E. | 0.18 | 0.17 | 0.36 | 0.47 | 0.05 | 0.32 | 0.59 | 0.86 |
| 22-d | Ctrl | Mean | 10.7 | 17.1 | 20.8 | 21.5 | 6.17 | 23.3 | 51.7 | 68.2 |
|  |  | S.E. | 1.98 | 3.93 | 4.26 | 3.70 | 2.13 | 4.73 | 10.2 | 13.2 |
|  | Trt | Mean | 6.88 | 11.8 | 15.0 | 15.7 | 3.84 | 15.4 | 35.4 | 47.3 |
|  |  | S.E. | 1.96 | 2.26 | 2.19 | 1.97 | 1.23 | 3.68 | 6.99 | 8.59 |

TABLE 7-continued

Mean (standard error) of ammonia daily emission rate (mg bird$^{-1}$ d$^{-1}$) and cumulative emissions (mg bird$^{-1}$) from broiler manure during a 4-d storage period (n = 12) with 10 air changes per hour (ACH) at 24° C.

| | | | Daily ER, mg bird$^{-1}$ d$^{-1}$ | | | | Cumulative Emission, mg bird$^{-1}$ | | | |
|---|---|---|---|---|---|---|---|---|---|---|
| | | | Storage time, day | | | | | | | |
| Age | Trt | | 1 | 2 | 3 | 4 | 1 | 2 | 3 | 4 |
| 30-d | Ctrl | Mean | 19.2 | 21.5 | 22.2 | 22.4 | 19.6 | 47.8 | 79.3 | 95.2 |
| | | S.E. | 3.30 | 1.53 | 2.18 | 2.52 | 5.47 | 8.33 | 8.86 | 8.83 |
| | Trt | Mean | 17.6 | 19.5 | 21.7 | 22.3 | 18.9 | 44.4 | 74.0 | 89.6 |
| | | S.E. | 4.98 | 2.90 | 1.75 | 2.24 | 7.41 | 12.6 | 14.0 | 13.4 |

The NH$_3$ ERs and cumulative emissions were significantly reduced over the 4-day storage period for the AP diet at 14-day (p≤0.04). The cumulative NH$_3$ emission of broiler manure decreased 23.8% after 4-day storage by the AP diet. Daily emission rate had the similar decreasing trend. There was no difference on NH$_3$ ER and cumulative emission between the two diets at 22- and 30-day due to large variations. However, there is tendency that the AP diet still reduces the ER and cumulative emission at 22 day (P=0.1).

The reduction rate of cumulative emissions with AP diet ranged from 31 to 38% at 22-d (Table 8).

TABLE 8

Reduction rate (percentage) of cumulative ammonia emissions during a 4-d storage period (n = 12)

| | Storage time, day | | | |
|---|---|---|---|---|
| Bird age | 1 | 2 | 3 | 4 |
| 14-d | 13.3 | 20.6 | 23.0 | 23.8 |
| 22-d | 37.8 | 33.9 | 31.7 | 30.7 |
| 30-d | 3.95 | 7.24 | 6.73 | 5.89 |

The efficacy of NH$_3$ emission reduction by the AP diet was age dependent during the testing period. The birds age significantly affect the NH$_3$ emission due to lower nitrogen content and pH in the manure of younger birds (P<0.01). This change could be related to the increasing trend of manure pH from 5.73 to 6.44. The ammoniacal N is in the form of NH$_4^+$, which is not volatile with low pH. Temperature also plays an important role on the NH$_3$ emissions since microbial activity and NH$_3$ volatilization are directly impacted by temperature. The outcome of the variable dietary efficacy could have stemmed from changes in manure properties, especially nitrogen content and pH, as the microbial activities varied considerably.

Under production conditions, the broiler houses with young birds tend to have higher NH$_3$ concentration at bird level due to limited ventilation. Lowering NH$_3$ emissions from broiler houses with young birds will help to establish healthy flocks and reduce the risk of disease breakout related to high NH$_3$.

EXAMPLE 3

This study is conducted to demonstrate that diets containing alkaline phosphatase added at 36 MU/ton in the treated group can reduce the NH$_3$ emissions under commercial conditions relative to a non-AP treated control, by verifying the efficacy of the additive selected from Example 2.

This field verification test was conducted using one house measuring 48 m×13.5 m (160 ft×45 ft) which is divided into 16 partitions, 6 m×6 m (20 ft×20 ft) each. The 6 rooms used in this study were managed separately, but share the same bird genetics and production stage, allowing better comparison the six flocks of birds with two different diets. Three rooms held flocks randomly signed with control diet, while the others contained birds with AP diet. Broilers over a 38-d growout period were raised in the house with control or treatment randomly assigned to house. Each room had an initial placement of 530 straight-run birds (mixed sex, Cobb×Cobb) with new wood shaving. The production rooms have insulated ceilings, box air inlets along the central alley, one brooding heater (30,000 BTU), one 0.3-m (12-in) centrifugal fan and one 0.6-m (24-in) diameter fan located on the side wall of the house. Independent environmental controllers coordinate control of air temperature, ventilation fan and heater operation, and lighting programs. Air temperature was monitored by a temperature sensor and logger (TMC6 and U12, Onset, Pocasset, Mass.).

Production performance data for both control and treatment rooms, including feed consumption, body weight, feed efficiency, and bird mortality, were collected. Bird live weight of each room was measured and recorded by a bird scale. The birds were fed and mortality was recorded daily. Three phase feeding strategy was used: starter from day zero to 13-d, grower from 14- to 31-d, and finisher from 32- to 38-d. The feed added into each room was weighed and recorded. At the end of the trial, the birds were weighed again and feed conversion ratio (FCR) was calculated.

A multi-point air sampling (Pak III, CAI, Orange, Calif.) and data acquisition system (SCADA3000, Sensaphone, Aston, Pa.) were used to monitor the control (Ctrl) and treatment (Trt) rooms with a 5-sec interval. The ON/OFF status of each fan was monitored by a AC-DC relay. The room static pressure was measured with a differential pressure sensor (T-VER-PXU-L, Onset, Pocasset, Mass.). A photoacoustic multi-gas analyzer (Innova Model 1412, CAI, Orange, Calif.) was used to measure the concentrations of NH$_3$, CO$_2$ and dew point temperature of the exhaust air. The Innova 1412 analyzer has been shown to be highly accurate, stable and responsive. Exhaust air samples from the fans in each house were drawn and analyzed to ensure good representation of the house air being exhausted to the atmosphere. The sampling port was placed between the two fans, 1.8 m (6 ft) above the floor and two feet apart from the wall. The air sampling interval was set to 140 sec per room (5 samples/room×28 sec/sample). In addition to the gaseous concentrations, the corresponding building ventilation rate will be measured by in-situ calibration of the exhaust fans with a FANS unit and continuous monitoring of operational state of the fans and the room static pressure (Equation 1).

$$VR = a + b \times SP \quad [1]$$

where VR=fan ventilation rate, m³/hr;
a, b=fan curve coefficients; and
SP=static pressure, Pa.

Three litter samples were taken from each room for nutrient and chemical analysis, including ammonia nitrogen ($NH_3$—N), total kjeldahl nitrogen (TKN), moisture content, and pH. $NH_3$ emission rate was calculated with concentration and ventilation rate [Equation 2].

$$ER = VR/n \times (C_e - C_i) \times (17.031 \text{ g/mol})/(22.414 \text{ L/mol}) \quad [2]$$

where ER=emission rate, mg/bird-hr;
VR=ventilation rate, m³/hr;
$C_e$=exhaust $NH_3$ concentration, ppmv;
$C_i$=inlet $NH_3$ concentration, ppmv; and
n=bird number per room.

Daily $NH_3$ emission rate (ER) and cumulative emissions over the 38-d growout period for the two diets were calculated and used for the data analysis. The data from each diet were pooled and analyzed for the dietary and age effect. Statistical analysis was performed using JMP 9.0 (SAS Institute, Inc., Cary, N.C.). The significance of dietary effect was indicated as ** with P-value ≤0.05 and * with P-value ≤0.1.

Production Performances and Manure Properties

Production performances of the broilers from the two diets are shown in Table 9.

TABLE 9

| | BW, g/bird | FCR | Livability, % | $NH_3$—N, % | TKN, % | MC, % | pH |
|---|---|---|---|---|---|---|---|
| Ctrl | 2400 | 1.70 | 92.4 | 1.05 | 3.62 | 31.6 | 7.1 |
| Trt | 2421 | 1.72 | 91.4 | 1.13 | 3.29 | 33.2 | 7.3 |

* BW: marketed bird body weight; FCR: feed conversion ratio; MC: moisture content; TKN: total Kjeldahl nitrogen.

There was no significant difference between the two diets on body weight gain and livability. The birds with AP diet had better growth rate at ages of 32-d (P=0.08). However, the control birds had lower FCR than the treatment group (P=0.002). There was a clear trend that the growth curve of the treatment dropped which may be caused by the changing feed after 31-d of age. It shows that there is no difference between the two diets on $NH_3$—N, TKN, pH, and moisture content at the end of the 38-d monitoring.

Ammonia Emissions

Daily $NH_3$ emission rate (ER) and cumulative emissions over the 38-d growout period for the two diets were summarized and shown in Table 10.

TABLE 10

| Bird age | ER, mg/bird-d | | | | Cumulative Emission, g/bird | | | |
|---|---|---|---|---|---|---|---|---|
| | Mean | | s.e. | | Mean | | s.e. | |
| | Ctrl | Trt | Ctrl | Trt | Ctrl | Trt | Ctrl | Trt |
| 7 | 8.71 | 5.40 | 1.2 | 1.2 | 0.067 | 0.038 | 0.01 | 0.01 |
| 8 | 11.2 | 6.59 | 1.6 | 1.0 | 0.079 | 0.045 | 0.01 | 0.01 |
| 9 | 9.03 | 5.01 | 1.2 | 0.7 | 0.089 | 0.050 | 0.01 | 0.01 |
| 10 | 7.30 | 3.91 | 1.3 | 0.4 | 0.10 | 0.054 | 0.01 | 0.01 |
| 11 | 11.0 | 7.29 | 1.1 | 0.8 | 0.11 | 0.062 | 0.01 | 0.01 |
| 12 | 10.9 | 8.81 | 1.3 | 1.3 | 0.12** | 0.072 | 0.01 | 0.01 |
| 13 | 12.7 | 9.10 | 1.7 | 0.5 | 0.13** | 0.081 | 0.02 | 0.01 |
| 14 | 16.7 | 11.8 | 3.2 | 0.5 | 0.15** | 0.094 | 0.02 | 0.01 |
| 15 | 17.1* | 11.3 | 2.3 | 0.8 | 0.17** | 0.11 | 0.02 | 0.01 |
| 16 | 20.1 | 17.1 | 1.8 | 1.8 | 0.19** | 0.12 | 0.02 | 0.01 |
| 17 | 15.5* | 9.07 | 2.5 | 1.0 | 0.21** | 0.13 | 0.02 | 0.01 |
| 18 | 22.5 | 14.9 | 3.8 | 0.9 | 0.23** | 0.15 | 0.03 | 0.01 |
| 19 | 20.2 | 17.4 | 3.1 | 7.0 | 0.25** | 0.17 | 0.03 | 0.02 |
| 20 | 45.0 | 39.4 | 5.8 | 0.2 | 0.30** | 0.21 | 0.03 | 0.02 |
| 21 | 52.8 | 34.1 | 8.9 | 2.2 | 0.36** | 0.25 | 0.04 | 0.02 |
| 22 | 152 | 148 | 9.3 | 2.7 | 0.52** | 0.40 | 0.04 | 0.02 |
| 23 | 201 | 156 | 19.4 | 11.1 | 0.73** | 0.57 | 0.06 | 0.03 |
| 24 | 272 | 215 | 39.7 | 16.9 | 1.01** | 0.79 | 0.10 | 0.03 |
| 25 | 395 | 327 | 49.2 | 35.3 | 1.42** | 1.14 | 0.14 | 0.05 |
| 26 | 227 | 179 | 21.4 | 21.3 | 1.66** | 1.32 | 0.16 | 0.06 |
| 27 | 292 | 263 | 20.1 | 39.3 | 1.96** | 1.59 | 0.18 | 0.10 |
| 28 | 391 | 405 | 6.2 | 35.4 | 2.36* | 2.01 | 0.18 | 0.12 |
| 29 | 384 | 340 | 25.9 | 49.6 | 2.76* | 2.36 | 0.20 | 0.17 |
| 30 | 500 | 514 | 31.1 | 62.9 | 3.27* | 2.89 | 0.22 | 0.23 |
| 31 | 529 | 525 | 36.6 | 46.7 | 3.81 | 3.43 | 0.25 | 0.27 |
| 32 | 543 | 571 | 27.4 | 54.5 | 4.36 | 4.01 | 0.27 | 0.32 |
| 33 | 528 | 573 | 37.6 | 37.1 | 4.89 | 4.59 | 0.28 | 0.36 |
| 34 | 602 | 659 | 11.0 | 31.5 | 5.50 | 5.26 | 0.29 | 0.39 |
| 35 | 616 | 638 | 20.2 | 27.4 | 6.12 | 5.90 | 0.31 | 0.40 |
| 36 | 621 | 518 | 59.1 | 8.0 | 6.75 | 6.42 | 0.35 | 0.41 |
| 37 | 622 | 574 | 11.5 | 16.4 | 7.37 | 7.00 | 0.36 | 0.40 |
| 38 | 343 | 354 | 20.1 | 57.7 | 7.72 | 7.35 | 0.37 | 0.38 |

*P ≤ 0.1; **P ≤ 0.05.

The $NH_3$ emissions of AP diet were significantly lower than the control diet till 28-d at P≤0.05 level and 31-d at P≤0.1 level. The $NH_3$ emission reduction rate decreased from 40% at 12-d of age to 19% at 27-d of age and 10% at 31-d of age. Daily emission rate had the similar decreasing trend. The field test shows the similar results that the efficacy of $NH_3$ emission reduction by the AP diet was age-dependent in the previous lab study (Li, 2011). The bird age significantly affected the $NH_3$ emission due to lower nitrogen content and pH in the manure of younger birds. Under the production condition, litter will be reused the broiler houses with young birds tend to have higher $NH_3$ concentration at bird level due to limited ventilation. Lowering $NH_3$ emissions from broiler houses with young birds will reduce bird level $NH_3$ concentration and reduce the risk of disease breakout related to poor air quality with high $NH_3$ concentration.

Based on Examples 2 and 3, feeding AP additives to broiler birds was shown to have the following impact on $NH_3$ emissions and production performance:

1) No significant difference on bird body weight, livability, and litter properties was observed from AP diet during the 38-d grow out. The birds with AP diet had better growth rate. However, the control group had better feed conversion ratio.

2) AP diet reduced manure pH (P=0.05) at 22-d and lowered phosphorus by 6 and 7% at 14- and 22-d (P=0.02). There was a trend that AP diet could reduce $NH_3$—N and TKN in the manure.

3) $NH_3$ emission from fresh manure was significantly reduced by 23.8% over a 4-d period with AP diet at 14-d. The efficacy of $NH_3$ emission reduction by the AP diet was age-dependent during the three testing period. The overall $NH_3$ emission reduction rates for the 4-d period were 5.9% from 30-d birds and 30.7% from 22-d birds.

4) The efficacy of $NH_3$ emission reduction by the AP diet under the field condition was age-dependent during the 38-d grow out period. The $NH_3$ emission was significantly reduced by 19% at 27-d of age and 10% at 31-d of age. The overall $NH_3$ emission reduction rates for the 38-d period were 4.7%.

5) These results indicate that the AP diet could help young broilers utilize and digest the nitrogen and phosphorus, which leads to better growth rate and less nutrient loss through excretion. Both lower pH and nitrogen content in manure could deter and prevent the formation of gaseous $NH_3$ in the manure and reduce the $NH_3$ emission.

EXAMPLE 4

A dose-escalation trial was conducted in turkeys. The experiment was designed as a randomized block design, with four dietary treatments (control and three different levels of alkaline phosphatase) randomly assigned among 4 blocks of 12 battery cages (pens) each. Turkeys were fed these diets ad libitum until 4 weeks. On day 24 of age of the birds, manure was collected. The manure was analyzed as described in Examples 1 and 2 above.

The test diets included alkaline phosphatase at four different levels: A: 0 (control); B: 22 MU/ton feed; C: 49 MU/ton feed; and D: 74 MU/ton feed (1 MU=120,000 IU). The diet was a typical starter diet supplemented with nutrients, as shown below.

| Description Ingredients | Starter diet Percent |
|---|---|
| CARGILSBM | 42.414 |
| CORN 2010 | 34.741 |
| DDGS | 6.000 |
| POULTRY MEAL | 5.000 |
| POULTRY FAT | 3.990 |
| DICALP 18.5 | 2.959 |
| Celite | 2.000 |
| LIMESTONE | 1.200 |
| ALIMET | 0.403 |
| MICRO SALT | 0.322 |
| LYSINE | 0.316 |
| CHOLINE CHLORIDE 60% | 0.192 |
| NCSU TRACE MINERAL PREMIX [2] | 0.200 |
| NCSU VITAMIN PREMIX [2] | 0.150 |
| SODIUM SELENITE PREMIX [1] | 0.050 |
| L-THREONINE | 0.063 |
| Total % | 100.00 |

[1] NaSeO3 premix provided 0.3 mg Se/kg of complete feed
[2] Each kilogram of mineral premix (.1% inclusion) supplied the following per kg of complete feed: 60 mg Zn as $ZnSO_4H_2O$; 60 mg Mn as $MnSO_4H_2O$; 40 mg Fe as $FeSO_4H_2O$; 5 mg Cu as $CuSO_4$; 1.25 mg I as $Ca(IO_3)_2$; 1 mg Co as $CoSO_4$.
[3] Each kilogram of vitamin premix (.1% inclusion) supplied the following per kg of complete feed: vitamin A, 13,200 IU; cholecalciferol, 4,000 IU; alpha-tocopherol, 66 IU; niacin, 110 mg; pantothenic acid, 22 mg; riboflavin, 13.2 mg; pyridoxine, 8 mg; menadione, 4 mg; folic acid, 2.2 mg; thiamin, 4 mg; biotin, 0.253 mg; vitamin B12, 0.04 mg; ethoxyquin, 100 mg.

| Nutrients | Unit | |
|---|---|---|
| Weight | KG | 1.0000 |
| DRY MATTER, % | PCT | 90.6418 |
| ME POULTRY, KCAL/KG | KCAL/KG | 2950 |
| CRUDE PROTEIN, % | PCT | 28.50 |
| MOISTURE, % | PCT | 9.36 |
| CRUDE FAT, % | PCT | 6.88 |
| CRUDE FIBRE, % | PCT | 2.59 |
| CALCIUM, % | PCT | 1.45 |
| TOTAL PHOSPHORUS, % | PCT | 1.062 |
| AVAIL. PHOS. POULTRY | PCT | 0.800 |
| SODIUM, % | PCT | 0.180 |
| POTASSIUM, % | PCT | 1.290 |
| CHLORIDE, % | PCT | 0.324 |
| Na + K—Cl, MEQ/KG | MEQ/K.G | 317.23 |
| ARGININE, % | PCT | 1.9236 |
| DIG. ARG TURKEY, % | PCT | 1.8287 |
| LYSINE, % | PCT | 1.8500 |
| DIG. LYS TURKEY, % | PCT | 1.6924 |
| METHIONINE, % | PCT | 0.8165 |
| DIG. MET TURKEY, % | PCT | 0.7390 |
| MET + CYS, % | PCT | 1.2500 |
| DIG. TSAA TURKEY, % | PCT | 0.9767 |
| THREONINE, % | PCT | 1.1500 |
| DIG. THR TURKEY, % | PCT | 0.9487 |
| TRYPTOPHAN, % | PCT | 0.3244 |
| DIG. TRP POULTRY, % | PCT | 0.2820 |
| CHOLINE, MG/KG | MG/KG | 2720.0000 |

The data show a dose-response relationship across diets A, B, and D. The results achieved with Diet C did not fit the dose-response relationship, but still showed reduced $NH_3$ ER as compared to control.

Manure Properties

There was no significant difference among the three AP diets for manure properties (P at 0.05). However, there was a trend that the B, C, and D diets with AP had lower manure pH and TKN, which could change the metabolism and growth of bacterial populations and cause less $NH_3$ formation and volatilization. The fresh manure from D diet had the lowest pH of 5.83 compared to 6.37, 6.15, and 6.38 from A, B, and C diets, respectively. The TKN of B, C, and D were 2.45, 2.38, and 2.57%, which were lower than 3.61% from A diet.

Ammonia Emission and Reduction

The $NH_3$ ERs of D diet were the lowest over the 7-d storage period. There was no difference on $NH_3$ ER and cumulative emission among the four diets (P>0.05) due to large variation. The large variation of $NH_3$ emissions could be caused by the uneven moisture content of the manure samples. The manure moisture contents of all 48 samples varied for 54 to 83%. Although the dietary effect is not significant, the results still reveals that the $NH_3$ emission could be reduced while the mean emission values were compared. The overall $NH_3$ ER reduction varied from 6.5 to 40% for the B (20.6%), C (6.5%), and D (40%) diets compared to A diet after the 7-d storage time. The outcome of the variable dietary efficacy could have stemmed from changes in manure properties, especially moisture content and pH, as the microbial activities varied considerably. Under the commercial production condition, the large variation of $NH_3$ emission among the manure with different moisture level could be cancelled out. It suggested that the manure samples should be more uniform and manure sample collection should be more carefully carried out.

In summary, feeding additives to turkeys was shown to have the following impact on ammonia emission and manure properties:

1) Manure on B, C, and D diets (with AP) showed lower pH and total nitrogen content than the A diet (control).

2) There was no significant difference on $NH_3$ ER and cumulative emission among the four diets due to large variation caused by big range of manure moisture content. The turkeys with B, C, and D diets (AP) tended to have lower $NH_3$ emissions than the A diet (control).

3) The overall $NH_3$ emission reduction rates for the 7-d period were −6.5% from C diet and 40% for D diet.

EXAMPLE 5

The transition of a nursing pig to dry feed at weaning is a very stressful time in the life of the pig. In addition to adapting to a new dietary regime, the pig must adjust to a new group feeding structure and the potential disease challenge to its immune system.

Another challenge for the pork producer is environmental regulations currently focusing on whole farm nutrient balance especially on nutrients that can have an impact on water quality. Phosphorus, in particular, is a nutrient that is excreted in manure in excessive amounts and has become the limiting nutrient dictating how much manure can be applied to cropland. Normal corn contains P but only approximately 15% of the P is digestible when fed to the pig. Therefore, inorganic P must be added to the diet to meet the pig's requirements for P, and the non-digestible P in the diet is excreted.

There is a needed to evaluate the value of alkaline phosphatase in nursery pig diets based on pig growth, feed intake, feed efficiency and health. In addition, the availability of phosphorus in nursery pig diets and the amount of P excreted needs to be determined as the pig's gut develops post-weaning and diets continue to change. The objective of this study is to determine the nutritional and environmental value of alkaline phosphatase in nursery pig diets based on nutrient digestibility and excretion.

A metabolism trial is conducted to evaluate nutrient digestibility and excretion from nursery pigs fed alkaline phosphatase supplemented diets. Twelve barrows are used with six barrows per dietary treatment. Pigs are fed a phase 1 pelleted conventional corn-soy-whey based diet for 7 days post-weaning. Pigs are then blocked by weight and ancestry to one of two dietary treatments.

Pigs are housed in pairs in the metabolism pens for the first 6 days of the metabolism period, adjusting to the phase 2 experimental diets fed twice daily at near ad libitum before being split into individual metabolism crates and fed restricted intake for 4 days prior to initiating a 3-day total urine and fecal collection. During collection, pigs are housed in individual stainless steel metabolism crates (2.33×2.83 ft.) fitted with nipple waterers. Screens and collection pans are placed beneath the crates to allow for separate and total urine and feces collection. Urine collection buckets are acidified with 100 mL 10% HCl to prevent ammonia volatilization.

The 4 days prior and during the 3 day collection period, pigs are fed twice daily at 07:30 and 17:00 at a rate of 9% of $BW^{0.75}$. Each morning of the collection, total orts, urine, and feces are collected, measured, and frozen at −20 C for later analysis. Daily samples from each pig are pooled for later analysis. Feces are thawed and blended with deionized water to make a 50:50 by weight slurry that is blended and then sub-sampled with 1 sample kept as a fecal slurry for the Nitrogen assays and a sample that is freeze dried and was used for all other nutrient assays.

Diets are ground through a 1 mm screen in a Wiley Mill (Thomas Scientific, Swedesboro, N.J.) prior to analysis. Dry matter is determined following a 16 h drying period at 100° C. Total N (Nelson and Sommers, 1972) and AmmN (Bremner and Keeney, 1965) are determined by micro-Kjeldahl procedures. Total P are determined colormetrically (Murphy and Riley, 1962) using a Beckman Du-6 Spectrophotometer (Beckman Coulter, Irvine, Calif.). Diet, fecal, and urine energies are determined by bomb calorimeter. Urine energy is determined by drying 4 mL of urine on sulka floc in the energy capsule and then combusting the sulka floc and urine in the bomb calorimeter and then determining the urinary energy by difference from the sulka floc treated with deionized water.

Pig was the experimental unit. The GLM procedure of SAS is used to determine statistical differences between treatments. Statistical significances are indicated by P<0.05 while statistical trends are indicated by P<0.10. Two experimental diets were used during the metabolism study: 1) Control, and 2) Control+60 MU AP. These diets allowed for a comparison between conventional and AP supplemented diets, and are noted below.

Phase 2 Metabolism Diets

| Ingredient, % | Control | Control + 60 MU AP |
|---|---|---|
| Corn | 40.485 | 40.485 |
| SBM, 48% CP | 22.330 | 22.330 |
| Swine Grease | 1.000 | 1.000 |
| Limestone | 0.420 | 0.420 |
| Monocalcium Phosphate | 0.300 | 0.300 |
| Vitamin Premix | 0.250 | 0.250 |
| Trace Mineral Premix | 0.150 | 0.150 |
| Selenium Premix | 0.050 | 0.050 |
| Salt | 0.300 | 0.300 |
| Plasma Protein | 2.500 | 2.500 |
| SD Blood Meal | 2.000 | 2.000 |
| Fish Meal | 4.000 | 4.000 |
| Poultry Meal-NRC | 4.000 | 4.000 |
| Dried Whey | 20.000 | 20.000 |
| Lysine-HCL | 0.100 | 0.100 |
| DL-Methionine | 0.170 | 0.170 |
| L-Threonine | 0.070 | 0.070 |
| Carbadox-2.5 | 1.000 | 1.000 |
| Chromic Oxide | 0.375 | 0.375 |
| Corn TRT Premix | 0.500 | 0.500 |
| Total | 100.000 | 100.000 |
| Calculated Nutrients | | |
| ME, kcal/kg | 3295.10 | 3295.10 |
| CP, % | 25.48 | 25.48 |
| Total Lysine, % | 1.680 | 1.680 |
| Digestible Lysine, % | 1.427 | 1.427 |
| SID Lysine, % | 1.500 | 1.500 |
| Dig. Methionine, % | 0.504 | 0.504 |
| Dig. Met + Cys, % | 0.835 | 0.835 |
| Dig. Threonine, % | 0.894 | 0.894 |
| Dig. Tryptophan, % | 0.247 | 0.247 |
| Dig. Isoleucine, % | 0.821 | 0.821 |
| Dig. Valine, % | 1.038 | 1.038 |
| Ca, % | 0.850 | 0.850 |
| P, % | 0.743 | 0.743 |
| Avail. P, % | 0.500 | 0.500 |
| Analyzed Composition | | |
| CP, % | 23.5 | 23.7 |
| P, % | 0.57 | 0.61 |
| Gross Energy, kcal/kg | 3975 | 3987 |
| Dry matter, % | 88.54 | 88.47 |

Results are provided in Table 11, entitled Effect of Alkaline phosphatase (AP) enzyme during the Early Nursery period on Dry Matter (DM), Energy, Nitrogen (N), and Phosphorus (P) digestibility and excretion.

TABLE 11

| AP, MU/ton | 0 | 60 | SE | Probability, P< |
|---|---|---|---|---|
| Initial BW, lb | 16.38 | 16.37 | 0.343 | 0.97 |
| Day 6 BW, lb | 19.57 | 19.63 | 0.484 | 0.92 |
| Final BW, lb | 24.05 | 24.53 | 0.522 | 0.53 |
| ADG d 0-6, lb/d | 0.531 | 0.544 | 0.054 | 0.86 |
| ADG d 6-13, lb/d | 0.640 | 0.700 | 0.025 | 0.12 |
| ADG d 0-13 lb/d | 0.590 | 0.628 | 0.029 | 0.38 |
| Total collection d10-13 | | | | |
| DM offered, g/d | 413.8 | 413.5 | 7.50 | 0.98 |
| DM intake, g/d | 372.4 | 398.9 | 12.91 | 0.18 |

TABLE 11-continued

| AP, MU/ton | 0 | 60 | SE | Probability, P< |
|---|---|---|---|---|
| Feces DM, g/d | 54.8 | 58.0 | 4.16 | 0.60 |
| Urine, mL/d | 551.4 | 631.9 | 83.46 | 0.51 |
| DM, % digested | 85.4 | 85.5 | 0.87 | 0.94 |
| Energy intake, kcal/d | 1480.3 | 1590.9 | 51.30 | 0.16 |
| Fecal Energy, kcal/d | 259.6 | 275.3 | 20.00 | 0.59 |
| Urinary Energy, kcal/d | 139.6 | 157.5 | 21.49 | 0.57 |
| Energy digested, % | 82.57 | 82.68 | 1.033 | 0.94 |
| Energy retained, % | 72.73 | 72.77 | 1.426 | 0.99 |
| Total N | | | | |
| Intake, g/d | 14.0 | 15.2 | 0.49 | 0.13 |
| Feces, g/d | 2.95 | 3.05 | 0.205 | 0.74 |
| Urine, g/d | 1.51 | 1.97 | 0.272 | 0.26 |
| N, % digested | 79.10 | 79.91 | 1.007 | 0.58 |
| N Retained, % intake | 68.33 | 66.84 | 2.140 | 0.63 |
| $NH_4$—N | | | | |
| Feces, g/d | 0.48 | 0.44 | 0.036 | 0.37 |
| P | | | | |
| Intake, g/d | 2.13 | 2.45 | 0.075 | 0.01 |
| Feces, g/d | 1.05 | 1.05 | 0.051 | 0.98 |
| Urine, g/d | 0.024 | 0.010 | 0.0122 | 0.42 |
| P, % digested | 50.53 | 57.14 | 1.805 | 0.03 |
| Retained, % intake | 49.23 | 56.75 | 1.900 | 0.02 |

There was no effect of diet on growth rate of the pigs during the first week of the diets being fed. However, during the second week (d 6-13), pigs fed the alkaline phosphatase tended (P<0.12) to grow slightly faster (9.4%) than the unsupplemented pigs (Table 11).

Alkaline phosphatase did not affect DM, Energy, or Nitrogen digestibility or excretion (P>0.26). However, due to the slightly higher feed intake and analyzed dietary phosphorus, pigs fed the AP diet had higher phosphorus intake (P<0.01), but similar fecal and urinary excretion of phosphorus. This resulted in pigs fed AP to have greater phosphorus digestibility (P<0.03) and retention (P<0.02) than pigs fed the control diet.

While not being bound by theory, there may be opportunity for the AP enzyme to improve the gut physiology of the weaned pig and this may lead to more efficient utilization of phosphorus.

We claim:

1. A method for reducing the environmental impact of animal waste, comprising orally administering to an animal a composition comprising an effective amount of an alkaline phosphatase comprising amino acids 33 to 572 of SEQ ID NO:1, wherein said alkaline phosphatase comprises serine at position 102 and reduces the amount of one or more detrimental compounds present in or released from animal waste, and one or more orally acceptable carriers, thereby reducing the environmental impact of animal waste.

2. The method of claim 1, wherein said detrimental compound is ammonia or phosphorous.

3. The method of claim 1, wherein said animal is a young animal.

4. The method of claim 1, wherein said animal is a chicken, a turkey, a swine, or a cow.

5. The method of claim 1, wherein the alkaline phosphatase is administered during one or more of the starter phase, the grower phase, and/or the finisher phase.

6. The method of claim 1, wherein the alkaline phosphatase is formulated in an animal feed or an animal feed additive.

7. The method of claim 1, wherein one or more additional active Ingredients are administered to said animal.

8. A composition suitable for oral administration to an animal comprising: an effective amount of an alkaline phosphatase comprising amino acids 33 to 572 of SEQ ID NO:1, wherein said alkaline phosphatase comprises serine at position 102 and reduces the amount of one or more detrimental compounds present in or released from animal waste, and one or more orally acceptable carriers.

9. The composition of claim 8, wherein said detrimental compound is ammonia or phosphorous.

10. The composition of claim 8, wherein said animal is a young animal.

11. The composition of claim 8, wherein said animal is a chicken, a turkey, a swine, or a cow.

12. The composition of claim 8, wherein said alkaline phosphatase is formulated to be orally administered during one or more of the starter phase, the grower phase, and/or the finisher phase.

13. The composition of claim 8, wherein said alkaline phosphatase is formulated in an animal feed or in an animal feed additive.

14. The composition of claim 8, wherein said composition comprises one or more additional active ingredients.

15. A method for increasing phosphorus digestion in an animal, comprising orally administering to said animal a composition comprising an effective amount of an alkaline phosphatase comprising amino acids 33 to 572 of SEQ ID NO: 1, wherein said alkaline phosphatase comprises serine at position 102, and reduces the amount of phosphorus present in or released from animal waste, and one or more orally acceptable carriers, thereby increasing digestion of phosphorus by said animal.

16. The method of claim 15, wherein said animal is a young animal.

17. The method of claim 15, wherein said animal is a chicken, a turkey, a swine, or a cow.

18. The method of claim 15, wherein said alkaline phosphatase is administered during one or more of the starter phase, the grower phase, and/or the finisher phase.

19. The method of claim 15, wherein said alkaline phosphatase is formulated in an animal feed or in an animal feed additive.

20. A method for reducing the amount of one or more detrimental compounds present in or released from animal waste, increasing animal feed conversion rate, increasing animal feed efficiency, and/or increasing animal growth rate, comprising orally administering to an animal an effective amount of a composition of claim 8.

21. An alkaline phosphatase comprising amino acids 33 to 572 of SEQ ID NO:1, wherein said alkaline phosphatase comprises serine at position 102 and reduces the amount of one or more detrimental compounds present in or released from animal waste when administered orally to an animal.

22. The alkaline phosphatase of claim 21, wherein said detrimental compound is ammonia or phosphorous.

* * * * *